(12) United States Patent
Rowe et al.

(10) Patent No.: US 9,352,118 B2
(45) Date of Patent: May 31, 2016

(54) MODULAR INTRODUCER AND EXCHANGE SHEATH

(75) Inventors: Douglas Rowe, San Jose, CA (US); Scott McIntosh, Sunnyvale, CA (US); Dawn Ma, San Jose, CA (US); Laveille Kao Voss, Belmont, CA (US)

(73) Assignee: ABBOTT LABORATORIES, Abbott Park, IL (US)

( * ) Notice: Subject to any disclaimer, the term of this patent is extended or adjusted under 35 U.S.C. 154(b) by 363 days.

(21) Appl. No.: 12/724,889

(22) Filed: Mar. 16, 2010

(65) Prior Publication Data

US 2010/0268163 A1 Oct. 21, 2010

Related U.S. Application Data

(63) Continuation-in-part of application No. 11/427,301, filed on Jun. 28, 2006.

(60) Provisional application No. 60/695,464, filed on Jun. 30, 2005.

(51) Int. Cl.
*A61M 39/06* (2006.01)
*A61M 25/00* (2006.01)
(Continued)

(52) U.S. Cl.
CPC ....... *A61M 25/0014* (2013.01); *A61M 25/0662* (2013.01); *A61M 39/06* (2013.01); *A61B 17/3462* (2013.01); *A61M 25/0075* (2013.01); *A61M 25/0097* (2013.01); *A61M 2025/0098* (2013.01)

(58) Field of Classification Search
CPC ............ A61M 39/06; A61M 39/0606; A61M 39/0613; A61M 2039/062; A61M 2039/0626; A61M 2039/0633; A61M 2039/0673; A61M 2039/426; A61M 2039/2433; A61M 2039/244; A61M 2039/2446; A61M 2039/2453; A61M 2039/246; A61M 2039/24662; A61M 25/0075; A61M 25/0097; A61B 17/3462; A61B 17/3498
USPC ............ 600/184, 154; 604/104, 167.03, 256, 604/167.02, 167.04, 264; 215/247; 251/149.1
See application file for complete search history.

(56) References Cited

U.S. PATENT DOCUMENTS

| 883,583 A | 3/1908 | Stallsmith |
| 1,696,018 A | 12/1928 | Schellberg |

(Continued)

FOREIGN PATENT DOCUMENTS

| EP | 0450221 | 10/1991 |
| JP | 3289967 | 12/1991 |

(Continued)

OTHER PUBLICATIONS

U.S. Appl. No. 11/427,308, Sep. 15, 2010, Office Action.
(Continued)

*Primary Examiner* — Diane Yabut
(74) *Attorney, Agent, or Firm* — Workman Nydegger; Randy Shen

(57) ABSTRACT

In accordance with the present disclosure there is provided exemplary embodiments of an introducer sheath, wherein the introducer sheath may be formed of multiple components at least one of which may be integrally formed or resiliently assembled to form a single introducer sheath. One embodiment of the introducer sheath includes a hub and a flexible valve. The flexible valve member may be non-planar in a relaxed state.

15 Claims, 17 Drawing Sheets

(51) Int. Cl.
*A61M 25/06* (2006.01)
*A61B 17/34* (2006.01)

(56) References Cited

U.S. PATENT DOCUMENTS

| | | | |
|---|---|---|---|
| 2,548,602 A | 4/1951 | Greenburg | |
| 4,143,853 A * | 3/1979 | Abramson | 251/149.1 |
| 4,406,656 A | 9/1983 | Hattler et al. | |
| 4,411,655 A | 10/1983 | Schreck | |
| 4,451,256 A | 5/1984 | Weikl et al. | |
| 4,574,173 A | 3/1986 | Bennett | |
| 4,596,559 A | 6/1986 | Fleischhacker | |
| 4,601,713 A | 7/1986 | Fuqua | |
| 4,619,643 A | 10/1986 | Bai | |
| 4,747,833 A | 5/1988 | Kousai et al. | |
| 4,899,729 A | 2/1990 | Gill et al. | |
| 4,950,257 A | 8/1990 | Hibbs et al. | |
| 4,983,168 A | 1/1991 | Moorehead | |
| 5,106,054 A | 4/1992 | Mollenauer et al. | |
| 5,106,368 A | 4/1992 | Uldall et al. | |
| 5,176,652 A | 1/1993 | Littrell | |
| 5,176,659 A | 1/1993 | Mancini | |
| 5,180,372 A | 1/1993 | Vegoe et al. | |
| RE34,327 E | 7/1993 | Kreamer | |
| 5,244,619 A | 9/1993 | Burnham | |
| 5,250,033 A | 10/1993 | Evans et al. | |
| 5,320,611 A | 6/1994 | Bonutti et al. | |
| 5,354,280 A | 10/1994 | Haber et al. | |
| 5,423,774 A | 6/1995 | Fischell et al. | |
| 5,447,503 A | 9/1995 | Miller | |
| 5,464,398 A | 11/1995 | Haindl | |
| 5,466,230 A | 11/1995 | Davila | |
| 5,558,737 A | 9/1996 | Brown et al. | |
| 5,584,803 A | 12/1996 | Stevens et al. | |
| 5,647,846 A | 7/1997 | Berg et al. | |
| 5,674,240 A | 10/1997 | Bonutti et al. | |
| 5,693,025 A * | 12/1997 | Stevens | 604/167.03 |
| 5,749,889 A | 5/1998 | Bacich et al. | |
| 5,795,326 A | 8/1998 | Simán | |
| 5,823,961 A | 10/1998 | Fields et al. | |
| 5,827,227 A | 10/1998 | DeLago | |
| 5,910,155 A | 6/1999 | Ratcliff et al. | |
| 5,944,691 A | 8/1999 | Querns et al. | |
| 5,957,902 A | 9/1999 | Teves | |
| 5,964,730 A | 10/1999 | Williams et al. | |
| 5,968,009 A | 10/1999 | Simán | |
| 5,993,436 A | 11/1999 | Kitou et al. | |
| 6,183,443 B1 | 2/2001 | Kratoska et al. | |
| 6,190,357 B1 | 2/2001 | Ferrari et al. | |
| 6,192,568 B1 | 2/2001 | Kafrawy et al. | |
| 6,224,586 B1 | 5/2001 | Stephens | |
| 6,280,433 B1 | 8/2001 | McIvor et al. | |
| 6,312,374 B1 | 11/2001 | von Hoffmann | |
| 6,358,266 B1 | 3/2002 | Bonutti | |
| 6,416,499 B2 * | 7/2002 | Paul, Jr. | 604/256 |
| 6,419,624 B1 | 7/2002 | Burton et al. | |
| 6,450,987 B1 | 9/2002 | Kramer | |
| 6,497,721 B2 | 12/2002 | Ginsburg et al. | |
| 6,616,678 B2 | 9/2003 | Nishtala et al. | |
| 6,630,086 B1 | 10/2003 | Goral et al. | |
| 6,712,791 B2 | 3/2004 | Lui et al. | |
| 6,749,600 B1 | 6/2004 | Levy | |
| 6,827,710 B1 | 12/2004 | Mooney et al. | |
| 6,849,062 B2 | 2/2005 | Kantor | |
| 6,887,417 B1 | 5/2005 | Gawreluk et al. | |
| 6,923,788 B2 | 8/2005 | Kantor | |
| 6,945,990 B2 | 9/2005 | Greenan | |
| 7,144,386 B2 | 12/2006 | Korkor et al. | |
| 7,637,893 B2 * | 12/2009 | Christensen et al. | 604/167.04 |
| 7,699,864 B2 | 4/2010 | Kick et al. | |
| 7,713,193 B2 | 5/2010 | Nance et al. | |
| 7,727,179 B2 | 6/2010 | Barrett | |
| 7,762,995 B2 | 7/2010 | Eversull et al. | |
| 7,896,897 B2 | 3/2011 | Gresham et al. | |
| 7,967,830 B2 | 6/2011 | Ayala et al. | |
| 7,974,710 B2 | 7/2011 | Seifert | |
| 8,012,127 B2 | 9/2011 | Lieberman et al. | |
| 2001/0049499 A1 | 12/2001 | Lui et al. | |
| 2002/0010425 A1 | 1/2002 | Guo et al. | |
| 2002/0032459 A1 | 3/2002 | Horzewski et al. | |
| 2002/0072768 A1 | 6/2002 | Ginn | |
| 2002/0107482 A1 | 8/2002 | Rocamora et al. | |
| 2002/0183781 A1 | 12/2002 | Casey et al. | |
| 2003/0004537 A1 | 1/2003 | Boyle et al. | |
| 2003/0014015 A1 * | 1/2003 | Tansey et al. | 604/167.04 |
| 2003/0032941 A1 | 2/2003 | Boyle et al. | |
| 2003/0050604 A1 | 3/2003 | Lui et al. | |
| 2003/0158578 A1 | 8/2003 | Pantages et al. | |
| 2004/0102738 A1 * | 5/2004 | Dikeman et al. | 604/256 |
| 2004/0153122 A1 | 8/2004 | Palermo | |
| 2005/0027257 A1 | 2/2005 | Davey | |
| 2005/0059934 A1 | 3/2005 | Wenchell et al. | |
| 2005/0059990 A1 | 3/2005 | Ayala et al. | |
| 2005/0080430 A1 | 4/2005 | Wright, Jr. et al. | |
| 2005/0085841 A1 | 4/2005 | Eversull et al. | |
| 2005/0131447 A1 | 6/2005 | Wahr et al. | |
| 2007/0005001 A1 | 1/2007 | Rowe et al. | |
| 2007/0224309 A1 | 9/2007 | Mejlhede et al. | |
| 2008/0004569 A1 | 1/2008 | McCrystle et al. | |
| 2008/0004571 A1 | 1/2008 | Voss | |
| 2008/0051717 A1 | 2/2008 | Voss et al. | |
| 2009/0054874 A1 | 2/2009 | Barron et al. | |
| 2009/0221965 A1 | 9/2009 | Osypka | |
| 2009/0264832 A1 * | 10/2009 | Dikeman et al. | 604/247 |
| 2009/0270989 A1 | 10/2009 | Conner et al. | |
| 2010/0094392 A1 | 4/2010 | Nguyen et al. | |
| 2013/0338595 A1 | 12/2013 | Voss | |

FOREIGN PATENT DOCUMENTS

| | | |
|---|---|---|
| WO | WO 98/13083 | 4/1998 |
| WO | WO 98/29026 | 7/1998 |
| WO | WO 2004/037333 | 5/2004 |
| WO | WO 2005/018728 | 3/2005 |
| WO | WO 2007/005584 | 1/2007 |
| WO | WO 2008/002915 | 1/2008 |
| WO | WO 2009/120871 | 10/2009 |

OTHER PUBLICATIONS

U.S. Appl. No. 11/767,947, Aug. 20, 2010, Office Action.
U.S. Appl. No. 11/427,308, Oct. 25, 2011, Office Action.
U.S. Appl. No. 12/695,969, Jan. 24, 2012, Office Aciton.
U.S. Appl. No. 12/696,792, Nov. 10, 2011, Office Action.
U.S. Appl. No. 12/696,837, Dec. 19, 2011, Office Action.
U.S. Appl. No. 12/695,961, Feb. 13, 2012, Office Action.
U.S. Appl. No. 12/695,975, Feb. 13, 2012, Office Action.
U.S. Appl. No. 11/767,947, Feb. 3, 2011, Office Action.
U.S. Appl. No. 11/427,301, Oct. 27, 2010, Office Action.
U.S. Appl. No. 11/427,306, Oct. 21, 2010, Office Action.
U.S. Appl. No. 11/767,947, Feb. 27, 2012, Office Action.
U.S. Appl. No. 12/695,961, filed Jan. 28, 2010, Voss.
U.S. Appl. No. 12/695,969, filed Jan. 28, 2010, Voss.
U.S. Appl. No. 12/695,975, filed Jan. 28, 2010, Voss.
U.S. Appl. No. 12/696,792, filed Jan. 29, 2010, Voss.
U.S. Appl. No. 12/696,837, filed Jan. 29, 2010, Voss.
U.S. Appl. No. 60/695,464, filed Jun. 30, 2005, Rowe.
U.S. Appl. No. 60/695,602, filed Jun. 30, 2005, Voss.
Richard Vennix, Material properties of PTFE, Engineering Polymers/Polymers Data Sheets, Matbase,<<http://www.matbase.com/material/polymers/engineering/ptfe/properties>>Jan. 25, 2010.
Richard Vennix, Material Properties of PMMA, Commodity Polymers/Polymer Data Sheets, Matbase, <<http://www.matbase.com/materials/polymers/commodity/pmma/properties>>Jan. 25, 2010.
U.S. Appl. No. 11/427,301, Apr. 27, 2010, Office Action.
U.S. Appl. No. 11/427,306, Feb. 26, 2008, Office Action.
U.S. Appl. No. 11/427,306, Mar. 5, 2009, Office Action.
U.S. Appl. No. 11/427,306, Aug. 21, 2009, Office Action.
U.S. Appl. No. 11/427,306, Apr. 12, 2010, Office Action.
U.S. Appl. No. 11/427,308, Sep. 29, 2009, Office Action.
U.S. Appl. No. 11/427,308, May 11, 2010, Office Action.

(56) References Cited

OTHER PUBLICATIONS

U.S. Appl. No. 11/767,947, Jun. 2, 2009, Office Action.
U.S. Appl. No. 11/767,947, Nov. 12, 2009, Office Action.
U.S. Appl. No. 11/767,947, Mar. 31, 2010, Office Action.
U.S. Appl. No. 11/767,947, Jul. 8, 2011, Office Action.
U.S. Appl. No. 11/427,308, Mar. 29, 2011, Office Action.
U.S. Appl. No. 11/427,301, Jun. 8, 2012, Office Action.
U.S. Appl. No. 12/695,961, May 11, 2012, Office Action.
U.S. Appl. No. 12/695,975, May 11, 2012, Office Action.
U.S. Appl. No. 12/695,961, Sep. 21, 2012, Notice of Allowance.
U.S. Appl. No. 11/427,308, Jul. 19, 2012, Office Action.
U.S. Appl. No. 12/695,969, Jul. 20, 2012, Office Action.
U.S. Appl. No. 12/696,837, Jul. 19, 2012, Office Action.
U.S. Appl. No. 13/752,137, filed Jan. 28, 2013, Voss.
U.S. Appl. No. 13/835,570, filed Mar. 15, 2013, Voss et al.
U.S. Appl. No. 12/695,975, Oct. 5, 2012, Office Action.
U.S. Appl. No. 11/427,301, Mar. 11, 2013, Office Action.
U.S. Appl. No. 12/695,961, Jan. 9, 2013, Issue Notification.
U.S. Appl. No. 12/695,969, Dec. 24, 2012, Notice of Allowance.
U.S. Appl. No. 12/695,969, Apr. 24, 2013, Issue Notification.
U.S. Appl. No. 11/427,308, Apr. 23, 2014, Office Action.
U.S. Appl. No. 11/767,947, Nov. 27, 2013, Notice of Allowance.
U.S. Appl. No. 12/695,975, Feb. 25, 2014, Office Action.
U.S. Appl. No. 12/696,792, Dec. 27, 2013, Office Action.
U.S. Appl. No. 13/752,137, Mar. 10, 2014, Office Action.
U.S. Appl. No. 13/892,106, Mar. 26, 2014, Office Action.
U.S. Appl. No. 12/695,975, Jul. 14, 2014, Office Action.
U.S. Appl. No. 12/696,837, Apr. 25, 2014, Office Action.
U.S. Appl. No. 13/752,137, Jun. 23, 2014, Notice of Allowance.
U.S. Appl. No. 13/835,570, Jul. 28, 2014, Office Action.
U.S. Appl. No. 13/892,106, Aug. 12, 2014, Office Action.
U.S. Appl. No. 14/551,374, filed Nov. 24, 2014, Voss.
U.S. Appl. No. 12/695,975, Dec. 16, 2014, Office Action.
U.S. Appl. No. 12/696,792, Jan. 29, 2015, Office Action.
U.S. Appl. No. 12/696,837, Jan. 13, 2015, Office Action.
U.S. Appl. No. 13/892,106, Nov. 28, 2014, Office Action.
U.S. Appl. No. 11/427,301, May 19, 2015, Notice of Allowance.
U.S. Appl. No. 12/696,792, Jul. 28, 2015, Office Action.
U.S. Appl. No. 13/835,570, Mar. 19, 2015, Office Action.
U.S. Appl. No. 13/892,106, Apr. 30, 2015, Office Action.
U.S. Appl. No. 13/892,106, Jul. 15, 2015, Notice of Allowance.

* cited by examiner

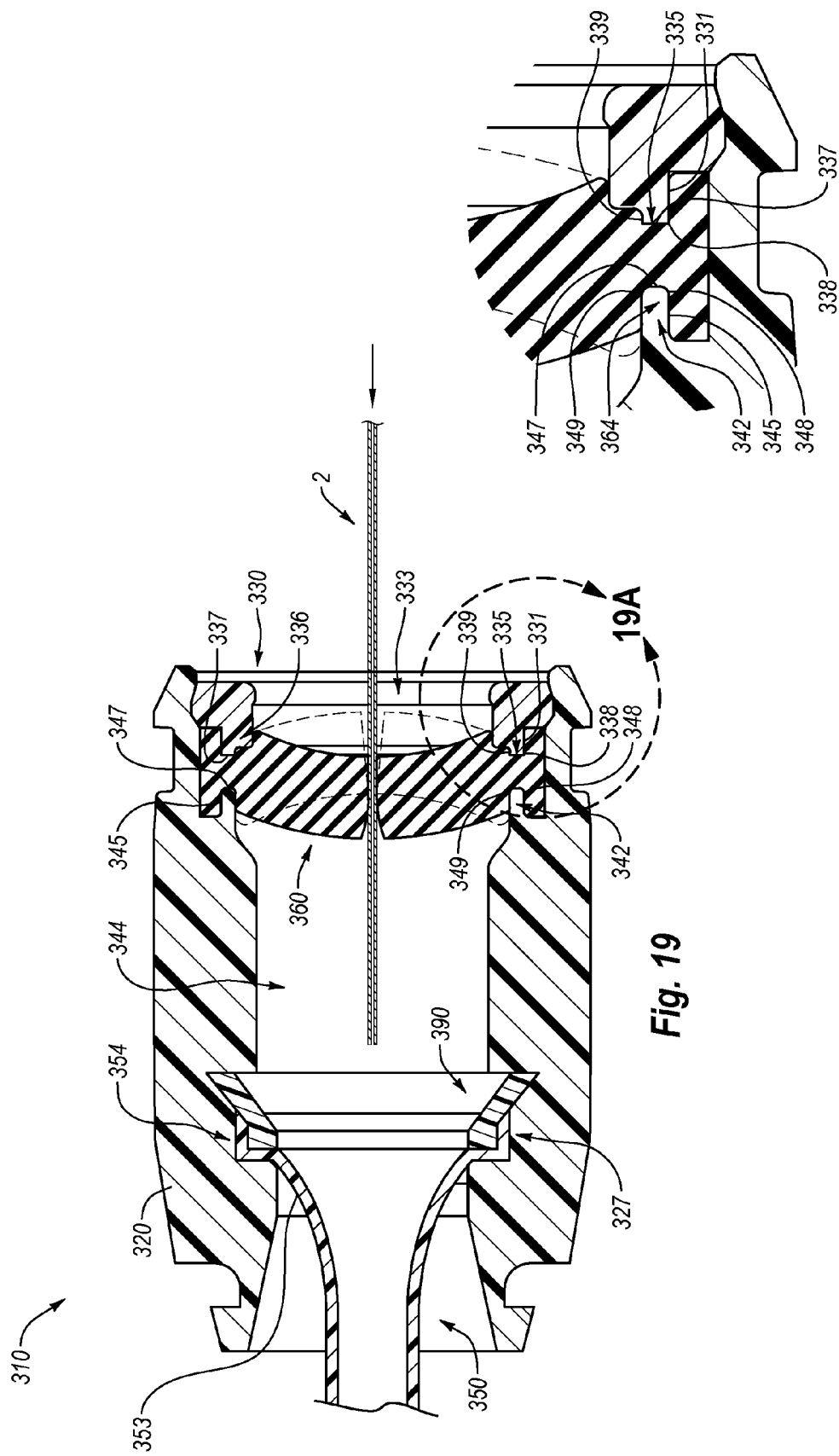

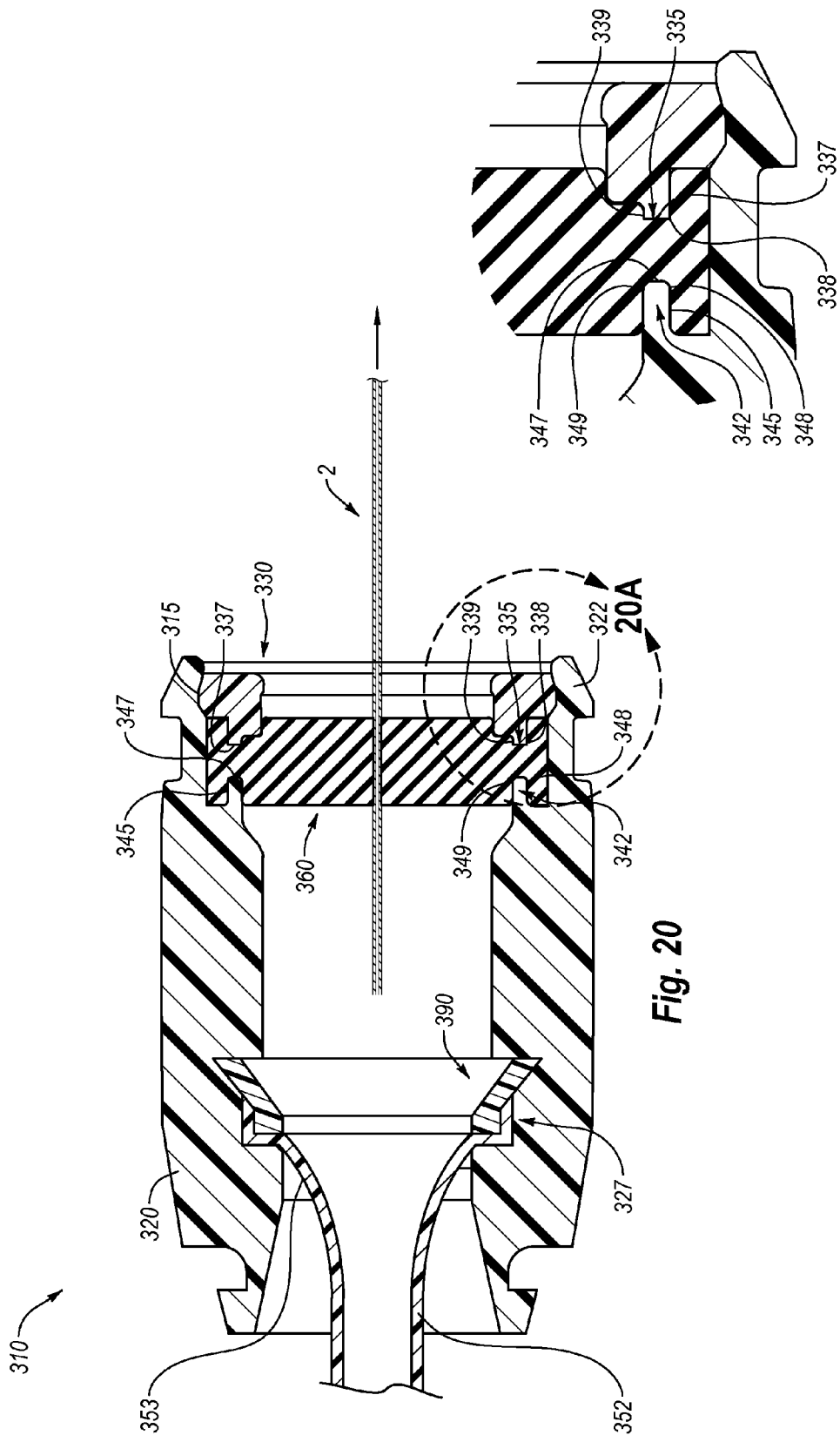

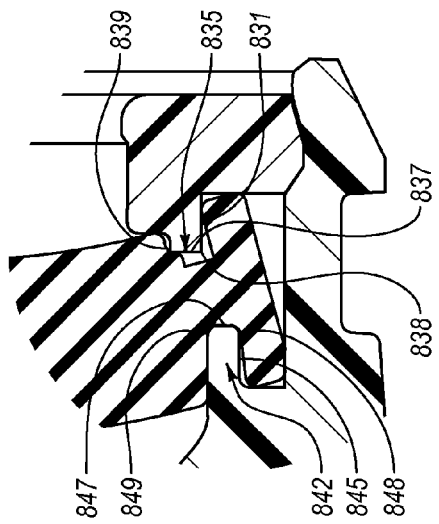
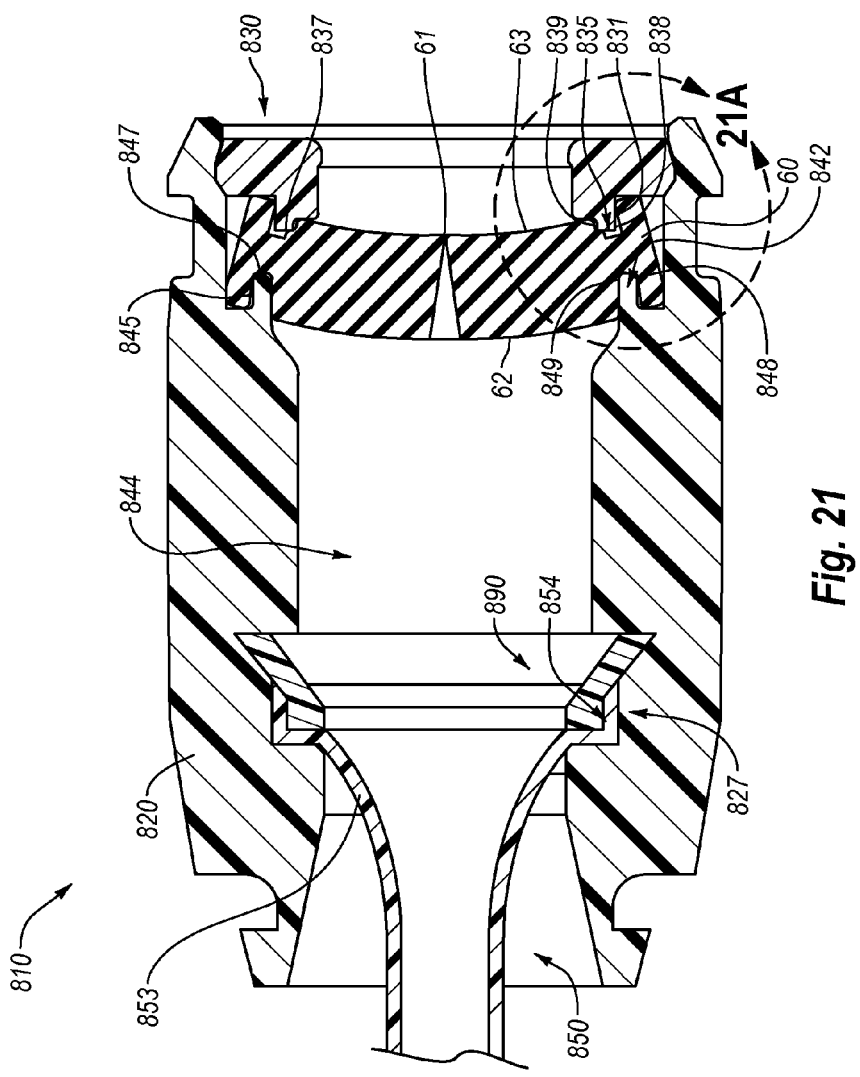

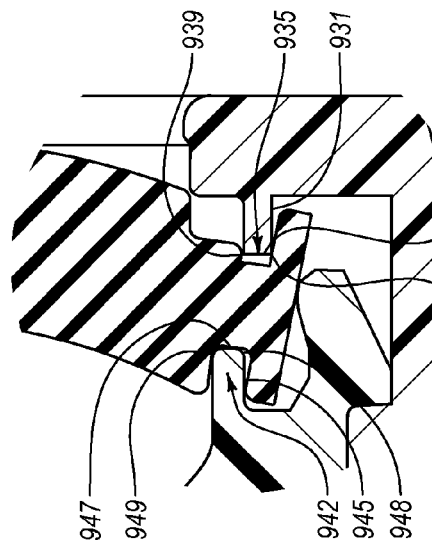
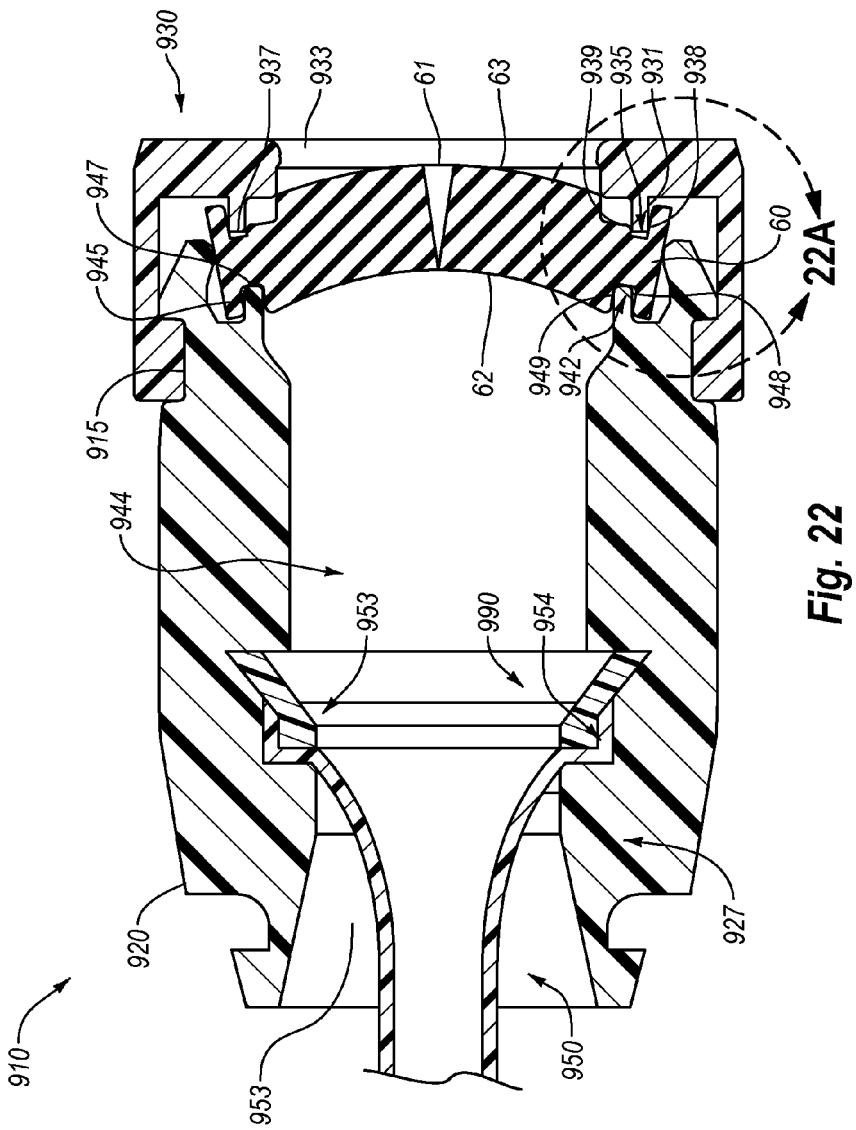

MODULAR INTRODUCER AND EXCHANGE SHEATH

CROSS-REFERENCE TO RELATED APPLICATIONS

This application is a continuation-in-part of U.S. patent application Ser. No. 11/427,301, filed Jun. 28, 2006, and entitled MODULAR INTRODUCER AND EXCHANGE SHEATH, which claims the benefit of U.S. Provisional Application Ser. No. 60/695,464, filed Jun. 30, 2005, and entitled MODULAR INTRODUCER SHEATH, the disclosures of which are hereby incorporated by reference in their entireties. This application also relates to U.S. patent application Ser. No. 12/695,961, filed Jan. 28, 2010, and entitled "INTRODUCER SHEATH AND METHODS OF MAKING," which is a continuation-in-part of U.S. patent application Ser. No. 11/427,306, filed Jun. 28, 2006, and entitled "INTRODUCER SHEATH" and relates to U.S. patent application Ser. No. 12/696,792, filed Jan. 29, 2010, and entitled "EXPANDABLE INTRODUCER SHEATH TO PRESERVE GUIDEWIRE ACCESS," which is a continuation-in-part of U.S. patent application Ser. No. 11/767,947, filed Jun. 25, 2007, and entitled "EXPANDABLE INTRODUCER SHEATH TO PRESERVE GUIDEWIRE ACCESS," which is a continuation-in-part of U.S. patent application Ser. No. 11/427,308, filed Jun. 28, 2006, and entitled "EXPANDABLE INTRODUCER SHEATH," the disclosures of which are each incorporated herein by this reference in their entireties.

BACKGROUND OF THE DISCLOSURE

1. The Field of the Invention

The present invention relates generally to medical devices and methods. More specifically, the present invention relates generally to introducer sheaths having a valve.

2. The Relevant Technology

A wide variety of introducer sheaths have been developed for medical use. Introducer sheaths are often used to access a vessel or artery to allow a surgical procedure to be performed. For example, introducer sheaths are often used for medical procedures that utilize catheters, such as angioplasty or stenting procedures. In practice, the introducer sheath is typically inserted into the patient's vasculature using the modified Seldinger technique. Under the Seldinger technique, a needle is first inserted into the vessel. A guidewire is then inserted through the needle and into the vessel. Next, the needle is removed and a sheath/dilator combination is advanced over the guidewire. The dilator is used to expand the puncture in the vessel to a size suitable to receive an introducer sheath. After the distal end of the sheath is disposed within the vessel, the dilator and guidewire are removed, thereby allowing access to the vessel.

Conventionally, introducer sheaths are formed of three or more components that require assembly: an elongated tubular member, a hub portion, and a hemostasis valve disposed within the hub portion. In some designs an introducer sheath may also include a strain relief member which is disposed adjacent the distal end of the hub and about the proximal end of the elongated tubular portion. A suitable example of such an assembly is shown in U.S. Pat. No. 5,807,350, which discloses an introducer sheath having a construction similar to that described above, the entirety of which is hereby incorporated herein by reference.

Introducer sheaths, such as that described above, are generally constructed of multiple pieces which must be assembled to form the sheath. In most cases, the distal end of the hub portion is molded over the elongated tubular member. While molding may produce a stronger part, there is the possibility of damaging a portion of the other components of the device during the process. Any such damage results in the entire device having to be thrown away. As a result, there is a need for a way to attach the proximal end of the tubular member to the distal end of the hub portion which still meets all of the requirements of the introducer sheath, including but not limited to forming a fluid seal and having sufficient strength between the attachment of the hub portion and the tubular member to remain attached, but does not require throwing the entire device away if a portion of the sheath is damaged during manufacturing or assembly. Thus, there is a need for a new introducer sheath having lower manufacturing costs and higher quality control while still retaining the important requirements for an introducer sheath.

BRIEF SUMMARY OF THE DISCLOSURE

These and other limitations are overcome by embodiments of the invention, which relates to medical devices and methods of use of, in particular, introducer sheaths. Embodiments of the invention provide several designs and methods of manufacture of the improved introducer sheath. One embodiment of the invention includes an introducer sheath formed as multiple components which can then be separately assembled to form an introducer sheath. In this embodiment, the components are assembled using resilient connections.

One embodiment of the introducer sheath includes a hub, a retaining member, and an elongated tubular member. The hub has a proximal end and a distal end with a lumen extending therebetween. In one embodiment, a portion of the lumen of the hub has a groove formed therein. The elongated tubular member has a distal end and a proximal end of which a portion is flared. The retaining member of the introducer sheath has a proximal end and a distal end configured to be received in the groove formed in the lumen of the hub. The distal end of the retaining member contacts the flared portion of the tubular member when the distal end of the retaining member is disposed in the groove such that the tubular member is retained within the lumen of the hub.

In one embodiment described above, a geometric pattern may be formed on the inner surface of the elongated tubular portion of the sheath, wherein the geometric pattern aids in splitting of the introducer sheath if desired.

The introducer sheaths disclosed herein are intended to be utilized in combination with a vessel closure device such as those shown in U.S. Pat. No. 6,197,042 and pending U.S. patent application Ser. No. 10/356,214, filed Aug. 8, 2004 entitled "Clip Applier and Methods of Use", which are both assigned to a common owner and are hereby incorporated by reference herein in their entireties.

An embodiment of an introducer sheath is described. The introducer sheath includes a hub having a proximal end and a distal end and a lumen extending therebetween. The hub includes a flexible valve member disposed in the proximal end of the hub. The flexible valve member has an aperture configured to receive a medical device. The introducer sheath includes an elongated tubular member having a proximal end and a distal end.

In some embodiments, the flexible valve member may be substantially non-planar in a relaxed state. The flexible valve member, in further embodiments, may be substantially concave in the relaxed state. In still further embodiments, the flexible valve member may be substantially planar in a relaxed state.

A further embodiment of an introducer sheath is described. The introducer sheath includes a hub having a proximal end and a distal end and a lumen extending therebetween. The hub includes a flexible valve member disposed in the proximal end of the hub. The flexible valve member has an aperture configured to receive a medical device. The introducer sheath includes an elongated tubular member having a proximal end and a distal end. The introducer sheath includes a cap disposed adjacent the flexible valve member and coupled to the proximal end of the hub.

In some embodiments, the flexible valve member may be substantially non-planar in a relaxed state. The flexible valve member, in further embodiments may be substantially concave in the relaxed state. In still further embodiments, the flexible valve member may be substantially planar in a relaxed state.

The cap, in some embodiments, may be configured such that upon being disposed over the flexible valve member, the cap provides a compressive force to the flexible valve member which causes the opening in the flexible valve member to be squeezed, thereby increasing the strength of the seal without reducing access to the lumen of the hub. In still further embodiments, the cap may be configured such that upon being disposed over the flexible valve member, the cap provides a compressive force to the flexible valve member which causes the flexible valve member to deform distally, thereby increasing the strength of the seal without reducing access to the lumen of the hub.

A still further embodiment of an introducer sheath is described. The introducer sheath includes a hub having a proximal end and a distal end and a lumen extending therebetween. The hub includes a flexible valve member disposed in the proximal end of the hub. The flexible valve member has an aperture configured to receive a medical device. The hub has an inner diameter. The introducer sheath includes an elongated tubular member having a proximal end and a distal end. The introducer sheath includes a cap disposed adjacent the flexible valve member and coupled to the proximal end of the hub. The cap includes a recess configured to receive the proximal end of the flexible valve member having an outer diameter. The outer diameter of the recess is smaller than the inner diameter of the hub.

In some embodiments, the flexible valve member may be substantially planar in a relaxed state. The cap, in further embodiments, may be configured such that upon being disposed over the flexible valve member. The cap may provide a compressive force to the flexible valve member which causes the flexible valve member to deform distally, thereby increasing the strength of the seal without reducing access to the lumen of the hub. In still further embodiments, the compressive force provided by the cap to the flexible valve member may be generated by the difference in the outer diameter of the recess of the cap and the inner diameter of the hub. The cap, in even further embodiments, may be retained in a retained position by an adhesive, a snap fit, or combinations thereof.

A yet further embodiment of an introducer sheath is described. The introducer sheath includes a hub having a proximal end and a distal end and a lumen extending therebetween. The hub includes a flexible valve member disposed in the proximal end of the hub. The flexible valve member has an aperture configured to receive a medical device. The hub has an inner diameter. The hub is overmolded with an elongated tubular member having a proximal end and a distal end. The introducer sheath includes a cap disposed adjacent the flexible valve member and coupled to the proximal end of the hub. The cap includes a recess configured to receive the proximal end of the flexible valve member having an outer diameter. The outer diameter of the recess is smaller than the inner diameter of the hub.

Additional features and advantages of the present invention will be set forth in the description which follows, and in part will be obvious from the description, or may be learned by the practice of the invention as set forth hereinafter. The features and advantages of the invention may be realized and obtained by means of the instruments and combinations particularly pointed out in the appended claims.

BRIEF DESCRIPTION OF THE DRAWINGS

To further clarify the above-recited and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIGS. 19 and 19A illustrate a further embodiment of an introducer sheath with a medical device inserted through the flexible valve member;

FIGS. 20 and 20A illustrate the embodiment of the introducer sheath shown in FIG. 19 with a medical device inserted through the flexible valve member and retracted to a retracted state; and FIGS. 21-21A and 22-22A illustrate additional embodiments of introducer sheaths with the flexible valve member of FIGS. 1-2, 4, 6, and 8 in a compressed state.

DETAILED DESCRIPTION

The following detailed description should be read with reference to the drawings in which similar elements in different drawings are numbered the same. The drawings, which are not necessarily to scale, depict illustrative embodiments and are not intended to limit the scope of the invention.

In accordance with the present invention, an introducer sheath formed as multiple components which can then be separately assembled to form an introducer sheath. In one embodiment, the components are assembled using a resilient engagement. In one embodiment, the introducer sheath comprises a hub having a proximal end and a distal end. The proximal end of the hub is configured to receive a flexible membrane or valve therein. The introducer sheath further includes an elongated tubular member generally extending from the distal portion of the hub. The elongated tubular member is generally centered with an axis of the hub.

Figure 1:
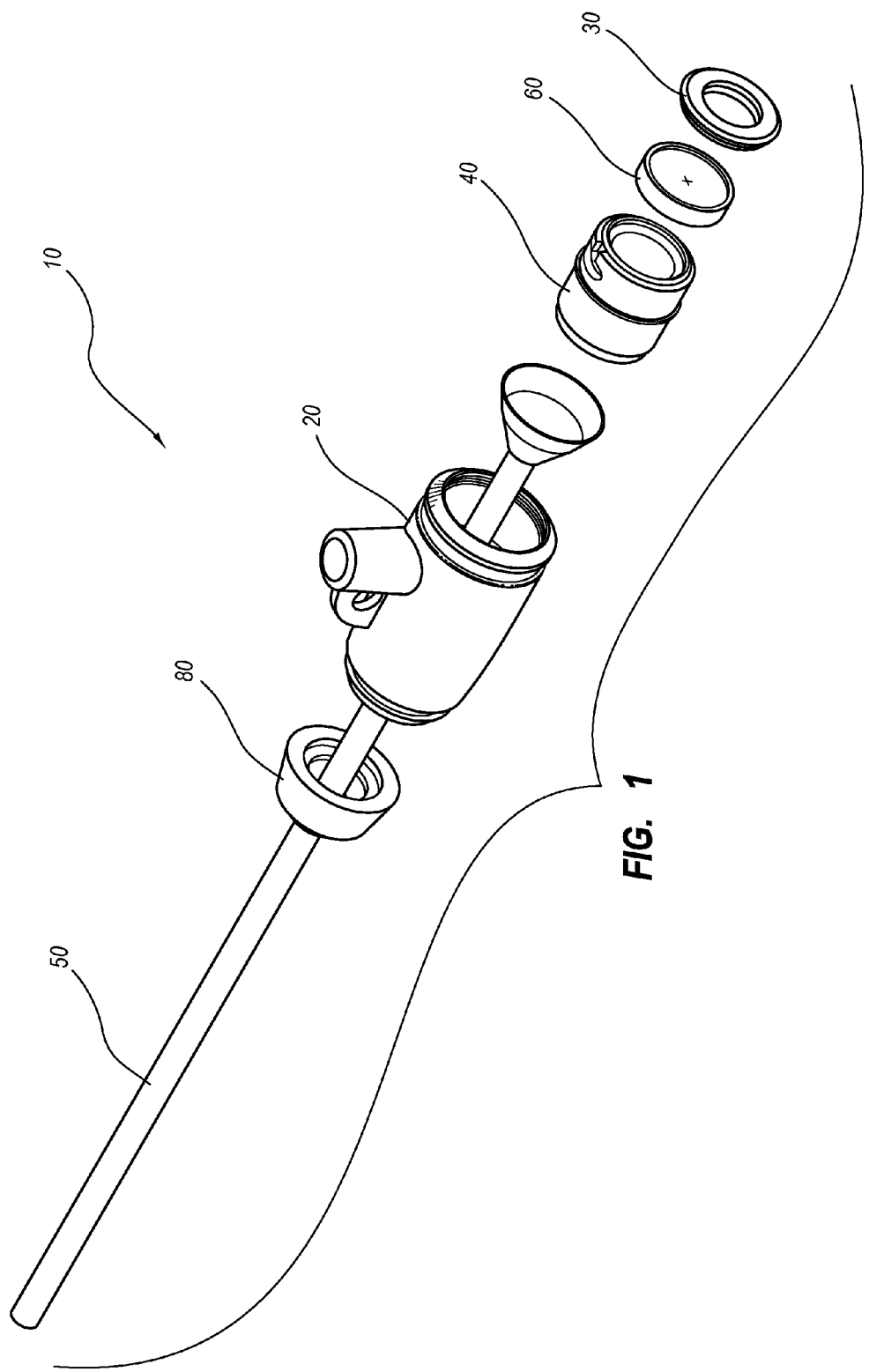
FIG. 1 is an exploded perspective view of an exemplary embodiment of an introducer sheath.
Figure 2:
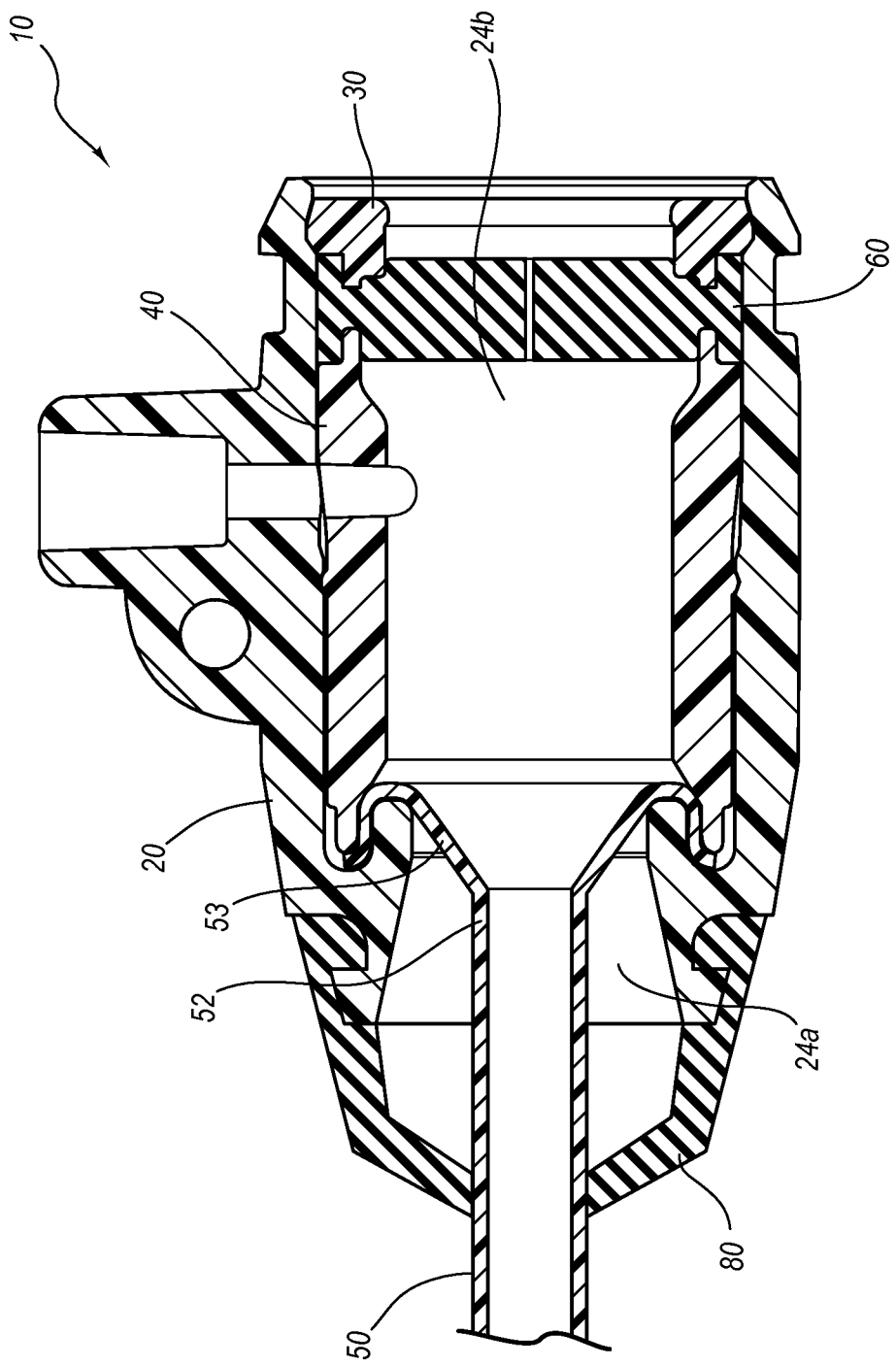
FIG. 2 is a partial cross-sectional view of one embodiment of an assembled introducer sheath in accordance with the present invention.

FIG. 1 depicts an exploded view of the individual components of one embodiment of an introducer sheath 10. FIG. 2 illustrates a cross-sectional view of an exemplary embodiment of an assembled introducer sheath 10 in accordance with the present invention. As shown in FIGS. 1 and 2, the introducer sheath 10 includes a hub 20, a cap 30, a retainer 40, and a generally elongate tubular member 50 extending outwardly from one end of the hub 20. The introducer sheath 10 also includes a flexible membrane or hemostasis valve 60. As illustrated in FIGS. 1 and 2, introducer sheath 10 includes an optional strain relief member 80.

Figure 3:
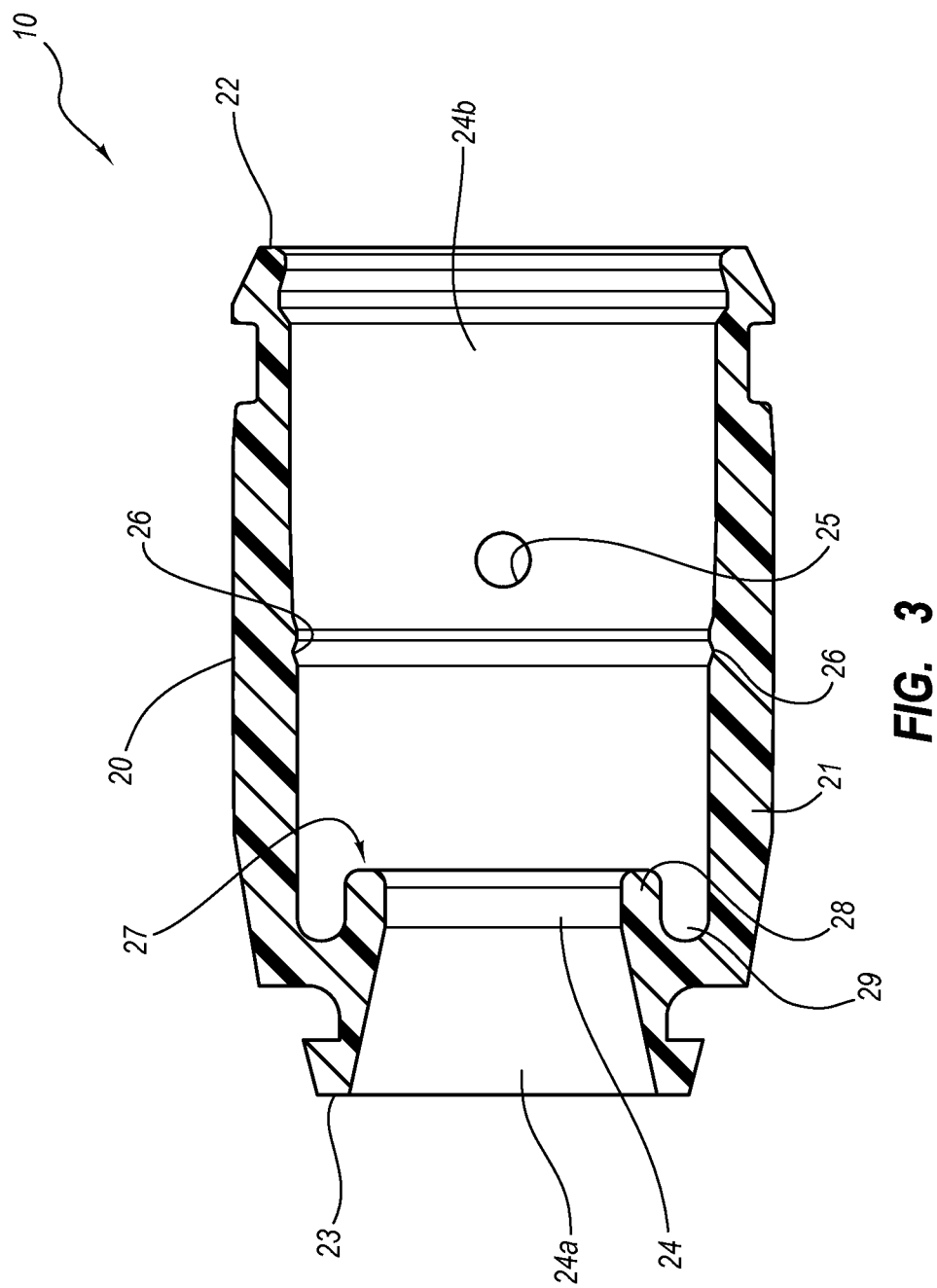
FIG. 3 is a cross-sectional view of one embodiment of a hub of the introducer sheath of FIG. 2 in accordance with the present invention.

As shown in further detail in FIG. 3, the hub 20 includes a main body 21 having a proximal end 22 and a distal end 23 and a central lumen 24 extending therebetween. In one possible embodiment, a port 25 may be provided in the side of the main body 21 of hub 20. The port 25 formed in the main body 21 of the hub 20 is in fluid communication with the central lumen 24 extending between the proximal end 22 and the distal end 23 of the main body 21 of hub 20.

In an exemplary embodiment depicted in FIG. 3, the central lumen 24 comprises a first lumen portion 24a and a second lumen portion 24b. The first lumen portion 24a and the second lumen portion 24b can have a common central axis. It will be appreciated by one skilled in the art that first lumen portion 24a and second lumen portion 24b are not required to have a common central axis. The first lumen portion 24a is proximate to the distal end 23 of the hub 20 while the second lumen portion 24b is proximate to the proximal end 22 of the hub 20. As illustrated in FIG. 2, the first lumen portion 24a is sized and configured so as to receive the proximal end 52 of the tubular member 50 therein. Similarly, the second lumen portion 24b is sized and configured to receive the retainer 40, the flexible member 60, and the cap 30 therein.

Returning to FIG. 3, in one embodiment the first lumen portion 24a and the second lumen portion 24a are of differing size. In this embodiment, the first lumen portion 24a is smaller than the second lumen portion 24b. As a result, the interior surface of the hub 20, which is defined by the diameters of the first lumen portion 24a and second lumen portion 24b has a shoulder area 27 in which the first lumen portion 24a transitions to the second lumen portion 24b. The shoulder area 27 may have various configurations as long as it is configured to cooperate with the proximal end 52 of the tubular member 50 and the distal end of the retainer 40 (see FIG. 2), as will be discussed in more detail below.

In an exemplary embodiment illustrated in FIG. 3, the shoulder area 27 includes a ridge 28 and a groove 29. The ridge 28 and the interior surface of the main body 21 of the hub 20 define the groove 29. The groove 29 may have various shapes and configurations as long as it is configured to receive the distal end of retainer 40 and cooperate with the proximal end 52 of the tubular member 50 as depicted in FIG. 2 and will be discussed in more detail below. In one embodiment depicted in FIG. 3, the groove 29 is a generally U-shaped channel. Alternatively, by way of example and not limitation, the groove 29 could be V-shaped, rounded, squared, tapered, or any combination thereof as long as it is configured to cooperate with retainer 40.

As illustrated most clearly in FIG. 3, in one exemplary embodiment ridge 28 is generally rectangular in shape. It will be appreciated that ridge 28 could have various shapes and configurations and perform the function thereof. By way of example and not limitation, ridge 28 could be square, round, or oval shaped or have an angular surface, or any combination thereof, as long as it is configured to cooperate with the proximal end of tubular member 50. In another embodiment, a portion of ridge 28 closest to the central axis of the hub 20 has been removed thereby forming an angled surface. In this embodiment, the angled surface of the ridge cooperates with the proximal end 52 of elongated tubular member 50.

As illustrated in FIG. 3, the second lumen portion 24b of the central lumen 24 formed in the hub 20 includes features formed therein. As will be described in detail below the features formed in the second lumen portion 24b are configured to receive various corresponding components of the introducer sheath 10.

Returning now to FIG. 2, as previously mentioned, the second lumen portion 24b of the central lumen 24 of the hub 20 is configured to receive the retainer 40 therein. The retainer 40 is configured to be detachably received within the central lumen 24 of the hub 20. More specifically, as illustrated in FIG. 2, the retainer 40 resiliently cooperates with the interior surface of the main body 21 of the hub 20. It will be appreciated that the outer surface of the retainer 40 could have various configurations as long as the retainer 40 is sized and configured to be received with second lumen portion 24b of central lumen 24. In one possible embodiment, the retainer 40 is also sized and configured so as to be resiliently retained within the second lumen portion 24b of the central lumen 24 of the hub 20.

Figure 4:
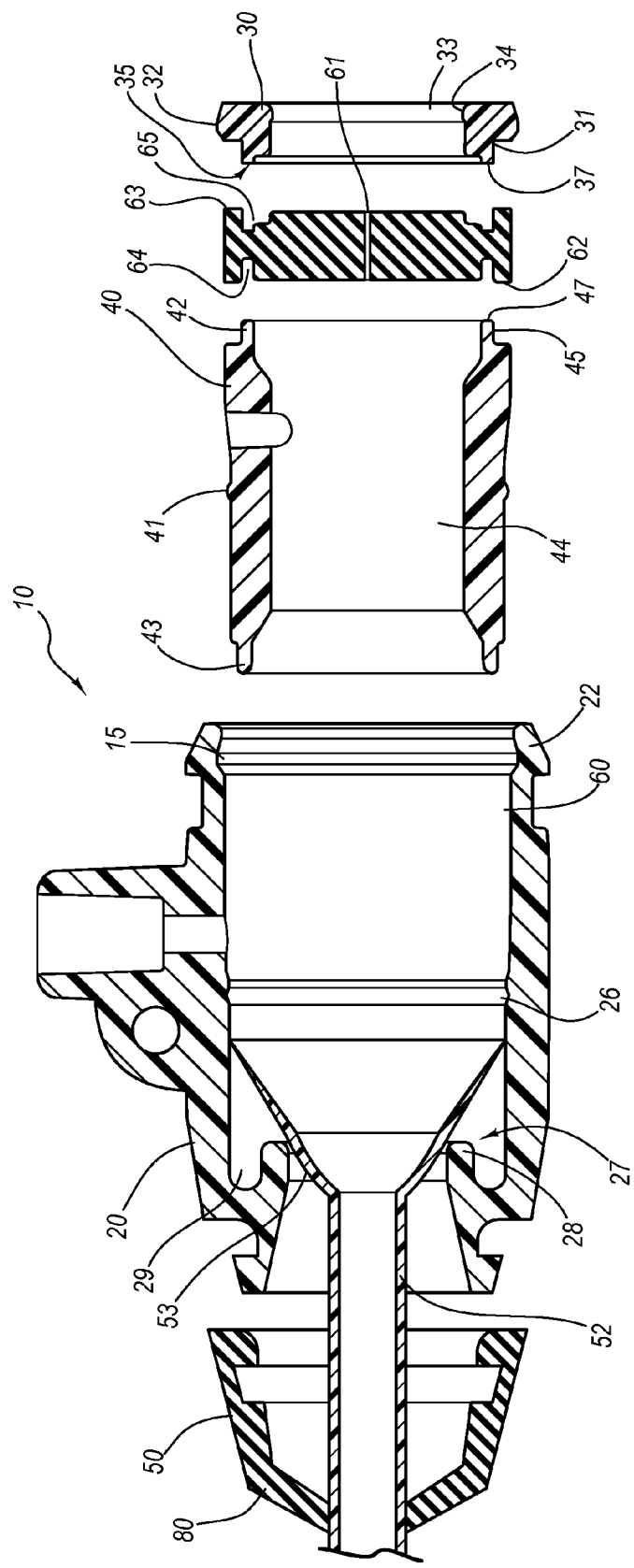
FIG. 4 is a partially exploded, cross-sectional view of the introducer sheath of FIG. 2 illustrating the individual components partially assembled to form the introducer sheath in accordance with the present invention.

FIG. 4 illustrates a cross-sectional view of one embodiment of the retainer 40 in accordance with the present invention. In one embodiment depicted in FIG. 4, the proximal end 42 of the retainer 40 is tapered outwardly so as to resiliently or frictionally engage the interior surfaces of the hub 20. In an exemplary embodiment, the retainer 40 includes locking features 41 formed in the outside surface of the retainer 40. The locking features 41 are configured to be received in corresponding locking features 26 formed in the interior surface of the main body 21 of the hub 20 as depicted in FIGS. 2 and 4.

In one embodiment illustrated, the locking features 41 and 26 are depicted as being generally rounded in shape. It will be appreciated that the locking features 41 and 26 could have various other configurations so long as they cooperate together in a resilient or frictional engagement and the locking features 41 are received into the corresponding locking features 26. By way of example and not limitation, the locking features 41 and 26 could be ovular, square, rectangular, angular, or various other shapes or combinations thereof. Further, the locking features 41 and 26 could be resilient members that slightly deflect until they snap into place. It will be appreciated by one skilled in the art that while in one embodiment retainer 40 is resiliently engaged in lumen 24 of the hub 20 by a snap-fit or frictional engagement, various other methods of attachment could be utilized, such as welding, adhesives, mechanical fasteners and the like.

One skilled in the art will also appreciate that while in the embodiment illustrated the locking features 41 of the retainer 40 protrude and are received in corresponding locking features 26 in the hub 20, they could be reversed such that the locking features 26 of the hub 20 are received into the locking feature 41 of the retainer. The importance is that the locking features 41 and 26 cooperate so as to resiliently engage and hold the retainer 40 in place in the hub 20.

Figure 6:
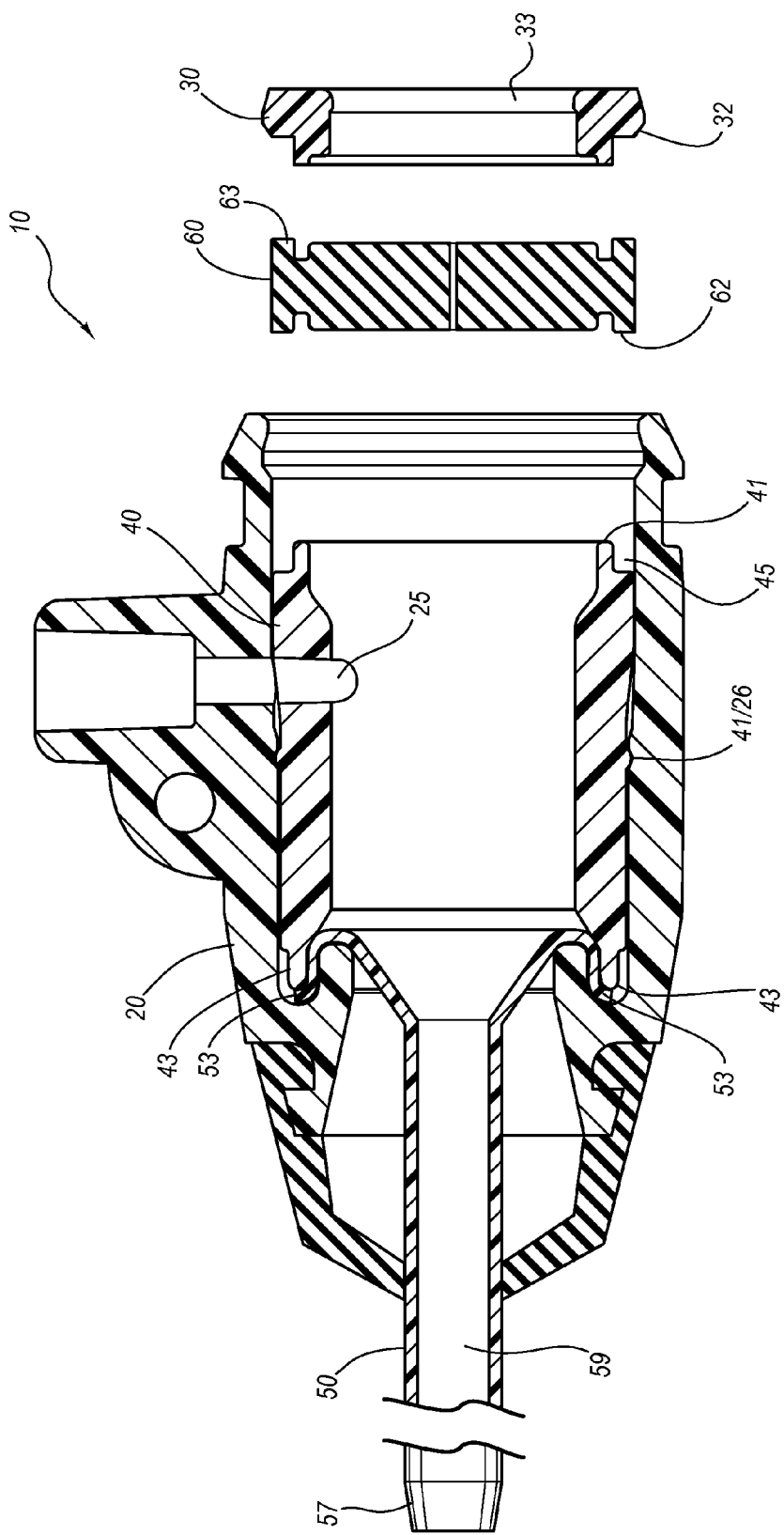
FIG. 6 is a partially exploded, cross-sectional view of the introducer sheath of FIG. 2 illustrating the components further partially assembled to form a sheath in accordance with the present invention.

As shown in FIG. 4, the retainer 40 includes a proximal end 42 and a distal end 43 with a lumen 44 extending therebetween. The proximal end 42 of the retainer 40 is configured to receive the flexible membrane or hemostasis valve 60 therein as shown in FIG. 2. As illustrated in FIGS. 2, 4, and 6, the distal end 43 of the retainer 40 is configured to be received within the shoulder area 27 of the hub 20. In particular, the distal end 43 of the retainer 40 is configured to be disposed in the groove 29 of the shoulder area 27. As illustrated in FIGS. 2 and 4, the distal end 43 of the retainer 40 is configured to cooperate with the proximal end 52 of the tubular member 50 and the groove 29 in the shoulder area 27 of the hub 20 so as to retain the proximal end 52 of the elongated tubular member 50, as will be described in greater detail below. In one embodiment, the interior surface of the distal end 43 of the retainer 40 has optional angular ridges or teeth-like features (not shown) formed there in that are configured to contact and engage proximal end of the tubular member 50.

Turning back to FIG. 4, the flexible membrane 60 includes an opening or a plurality of slits formed therein to form an opening 61. The opening 61 allows a medical device to pass through the flexible membrane 60. It will be appreciated by one skilled in the art that the opening 61 of the flexible membrane 60 may have various other configurations and perform the functions thereof. The flexible membrane 60 and the opening 61 are sized and configured to form a fluid tight seal about the medical device. Flexible membranes of this type are commonly referred to as hemostasis valves.

The flexible membrane 60 is configured to cooperate with the proximal end 42 of the retainer 40. More specifically, in one exemplary embodiment, the proximal end 42 of the retainer 40 has a recess 45 formed therein configured to receive the distal end 62 of the flexible membrane 60. It will be appreciated that the recess 45 could have various other configurations as long as it is configured to cooperate with the distal end 62 of the flexible membrane 60. In one embodiment depicted in FIG. 4, the recess 45 is a generally square shaped. Alternatively, by way of example and not limitation, the recess 45 could be rounded, oval, rectangular tapered, or any combination thereof as long as it is configured to cooperate with the distal end 62 of the flexible membrane 60.

As illustrated in FIG. 4, in one embodiment, correspondingly distal end 62 of the flexible membrane 60 has an opening 64 formed therein configured to cooperate with the proximal end 42 of the retainer 40. It will be appreciated by one skilled in the art that the distal end 62 of the flexible membrane 60, including opening 64, and the proximal end 42 of the retainer 40, including recess 45, could have various other configurations and shapes as long as they are configured to cooperate and have a sealing engagement. Alternatively, by way of example and not limitation, the opening 64 of the flexible membrane 60 and proximal end 42 of the retainer 40 could be U-shaped, round, square, oval, elliptical, tapered, or any combination thereof as long as they are configured to cooperate.

As shown in FIG. 2, the flexible membrane 60 is retained between the retainer 40 and the cap 30. An exemplary embodiment of the cap 30 of the present invention is illustrated in FIG. 4. In one embodiment, the cap 30 is configured to cooperate with the proximal end 63 of the flexible membrane 60. In particular, in this embodiment the exterior surface of the cap 30 has the recess 31 formed therein which is configured to receive the proximal end 63 of the flexible membrane 60. Similarly, the proximal end 63 of the flexible member 60 has an opening 65 formed therein configured to receive portion 36 of the cap 30. It will be appreciated by one skilled in the art that the distal portion 36 of the cap 30 and the opening 65 in the proximal end 63 of the flexible membrane 60 can have various other configurations and shapes as long as they are configured to cooperate and have a sealing engagement. Alternatively, by way of example and not limitation, that the distal portion 36 of the cap 30 and the opening 65 in the proximal end 63 of the flexible membrane 60 could be U-shaped, round, rectangular square, oval, elliptical, tapered, or any combination thereof as long as they are configured to cooperate.

It will be appreciated that the recess 31 could have various other configurations as long as the proximal end 63 of the flexible membrane 60 and the recess 31 are correspondingly shaped to cooperate. In one embodiment depicted in FIG. 4, the recess 31 is a generally square shaped. Alternatively, by way of example and not limitation, the recess 31 could be rounded, oval, rectangular tapered, or any combination thereof as long as it is configured to cooperate with the distal end 62 of the flexible membrane 60.

In one exemplary embodiment, the cap 30 when disposed over the flexible membrane 60 provides a compressive force (or stress) to the flexible membrane 60, wherein the compressive force (or stress) exerted on (or induced in) the flexible membrane 60 causes the opening 61 to be squeezed and thereby forming a more fluid tight seal therein. This compressive force (or stress) however may not reduce access to and/or increase forces necessary to pass a medical device through the opening 61 of the flexible membrane 60. Additionally, as described above, the compressive force (or stress) exerted on (or induced in) the flexible membrane 60 increases the sealing of the opening 61 in a static state, the compressive force (or stress) also increases the seal between the flexible membrane 61 and a medical device disposed through the opening 61 for the same reasons.

For example, the compressive force (or stress) exerted on (or induced in) the flexible membrane 60 may be an axial compressive force (or stress) that may cause the opening 61 to be squeezed and thereby forming a more fluid tight seal therein. As shown in FIG. 2, the compressive forces (or stresses) may be generally applied to (or induced in) both the proximal end 63 and the distal end 62 of the flexible valve member 60. In other embodiments, the forces (or stresses) may be applied to (or induced in) only the proximal end 63 or the distal end 62, the forces (or stresses) may be unevenly distributed to (or induced in) the proximal end 63 and/or the distal end 62, other forces (or stresses) may be applied to (or induced in) the proximal end 63 and/or the distal end 62, or combinations thereof.

In some embodiments, the orientation of the flexible valve member 60 in a relaxed state, a compressed state, a retracted state, or combinations thereof may be determined by the relationship between the distal end 35 of the cap 30 and the proximal end 42 of the retainer 40. The cap 30 may include a proximal engaging surface 37 and the retainer 40 may include a distal engaging surface 47. For example, as shown in FIG. 4, the recess 31 and the aperture 33 of the cap 30 may form the proximal engaging surface 37 and the recess 45 and the lumen 44 of the retainer 40 may form the distal engaging surface 47. The position of the proximal engaging surface 37 and the distal engaging surface 47 with respect to each other may determine the orientation of the flexible valve member 60.

Figure 8:
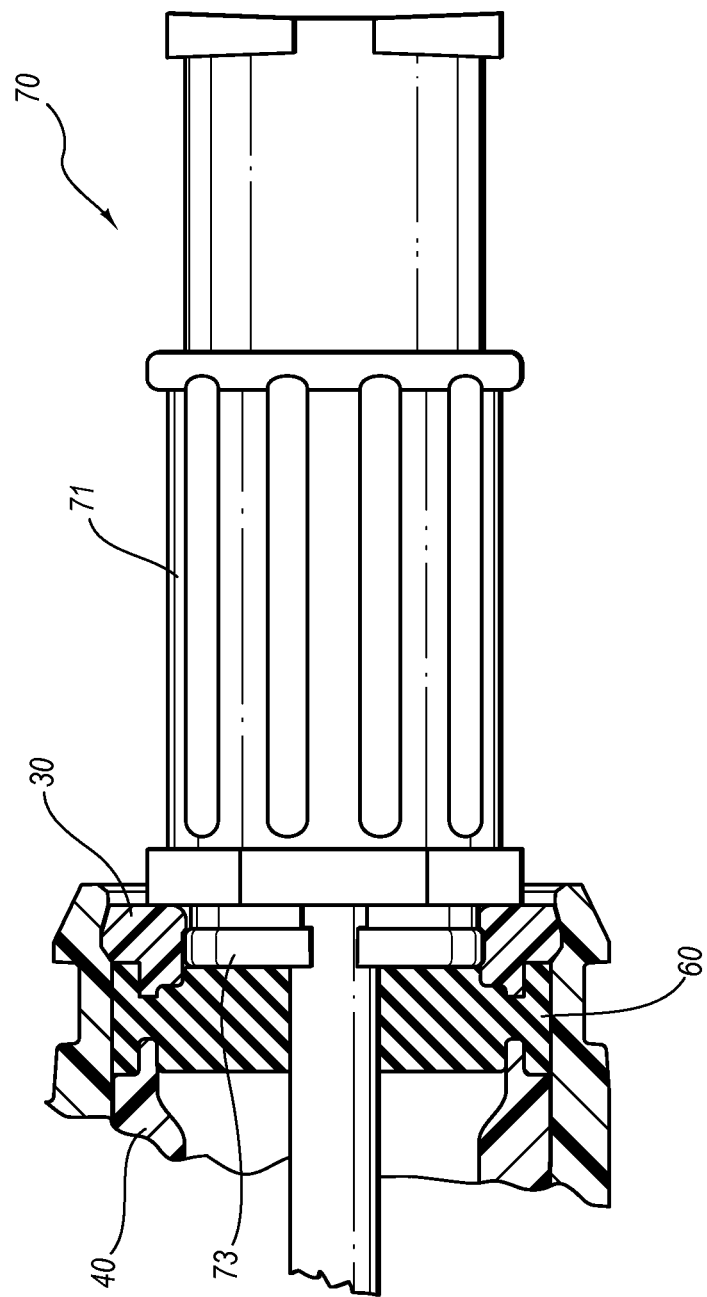
FIG. 8 is a partial cross-sectional, elevation view of the dilator of FIG. 7 attached to the introducer sheath of FIG. 2 in accordance with the present invention.

As shown in FIGS. 2, 4, 6, and 8, flexible valve member 60 may have a substantially planar (i.e. flat) configuration in a relaxed state and in a compressed state. For example, as shown in FIGS. 4 and 6, the distal end 62 and proximal end 63 are substantially coplanar (i.e. parallel when flat) and/or planar while in a relaxed state (i.e. not inserted into the sheath 10). In another example, as shown in FIGS. 2 and 8, the distal end 62 and proximal end 63 are substantially coplanar and/or planar while in a compressed state (i.e. inserted into the sheath 10). The opening 61 may have a constant cross-sectional dimension, such as the inner diameter, in the relaxed state.

The substantially planar configuration of the flexible valve member 60 in the relaxed and compressed states may be determined by the relationship between the proximal engaging surface 37 and the distal engaging surface 47. For example, as shown in FIGS. 2, 4, 6, and 8, the proximal engaging surface 37 and the distal engaging surface 47 have approximately the same inner diameter and approximately the same outer diameter causing the compressive forces (or stresses) to be generally evenly applied to (or induced in) both the distal end 62 and the proximal end 63 of the flexible valve member 60. Generally even application of forces (or stresses) to both the distal end 62 and the proximal end 63 of the flexible valve member 60 may result in a substantially planar configuration of the flexible valve member 60 in both the relaxed and compressed states.

As shown in FIGS. 2 and 4, the exterior surface 32 of the cap 30 is sized and configured to be received within the proximal end 22 of the hub 20. In one embodiment illustrated in FIG. 4, the exterior surface 32 of the cap 30 is slightly angled to form a protrusion so as to be received within a corresponding cutout 15 formed on the interior surface of the proximal end 22 of the main body 21 of the hub 20. As shown in FIG. 4 the proximal end 22 of the main body 21 of the hub 20 is configured so as to resiliently move to allow the exterior surface 32 of the cap 30 to be received within the cutout 15 formed therein. In another embodiment, the exterior surface 32 of the cap 30 includes a resilient protrusion which upon the cap 30 being inserted into proximal end of the retainer 40 locks the cap 30 in place. The proximal end 22 of the main body 21 of the hub 20 includes a corresponding cutout 15 configured to receive the resilient protrusion. In either embodiment, the exterior surface 32 of the cap 30 and the interior surface of proximal end of the hub 20 are configured to cooperate such that the cap resiliently snaps into place. It will be appreciated that the exterior surface 32 of the cap 30 can have various other configurations and shapes as long as it is configured to cooperate with the proximal end 22 of the hub 20. In one exemplary embodiment, proximal end 22 of the hub 20 and the exterior surface 32 cooperate form a seal.

It will be appreciated by one skilled in the art that while in one embodiment, retainer 40 is resiliently engaged in lumen 24 of the hub 20 by a snap-fit or frictional engagement, various other methods of attachment could be utilized, such as welding, adhesives, mechanical fasteners and the like.

Figure 5:
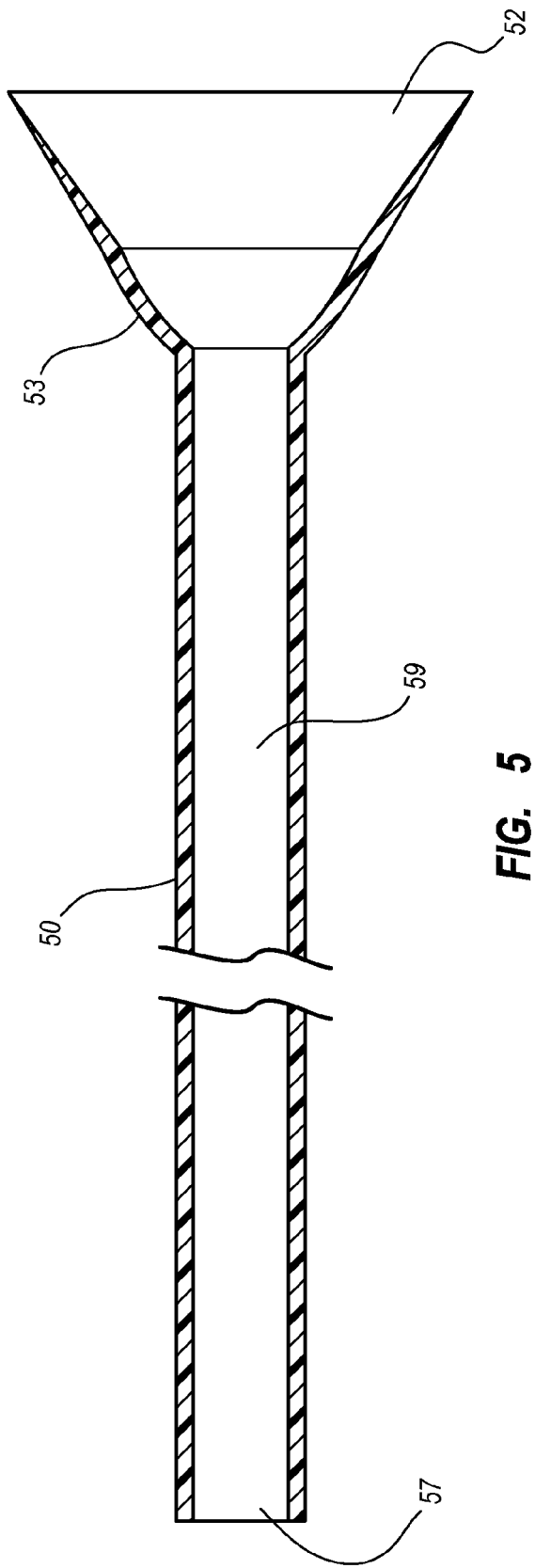
FIG. 5 a partial cross-sectional view of one embodiment of the elongated tubular member of the introducer sheath of FIG. 2 in accordance with the present invention.

FIG. 5 depicts an exemplary embodiment of the tubular member 50 in accordance with the present invention. The tubular member 50 includes a proximal end 52 and a distal end 57 with a lumen 59 extending between the two ends. In one embodiment illustrated in FIG. 5, the proximal end 52 of the tubular member 50 includes a flared portion 53 that has generally conical or flared configuration. The tubular member 50, including the flared portion 53, is comprised of a resilient flexible material. As previously mentioned the proximal end 52 of the tubular member 50 is configured to be received proximate to the distal end 23 of the hub 20 as illustrated in FIG. 4.

In particular, referring now to FIGS. 4 and 6, the flared portion 53 of the proximal end 52 of the tubular member 50 is configured to cooperate with the shoulder area 27 formed in the main body 21 of the hub 20 and the distal end 43 of the retainer 40. When the tubular member 50 is disposed in the central lumen 24 of the hub 20 and the retainer 40 is then inserted into the central lumen 24 of the hub 20, as illustrated in FIG. 6, the distal end 43 of the retainer 40 together with the ridge 28 and the groove 29 of the shoulder area 27 cooperate to retain the flared portion 53 of the distal end 52 of the tubular member 50.

It will be appreciated that the ridge 28 and the groove 29 of the shoulder area 27 of the hub 20, the distal end 43 of the retainer 40, and the flared portion 53 of the proximal end 52 of the tubular member 50 are one possible embodiment of a means for retaining tubular member 50 in the hub 20 in sealing engagement. The retaining means may also consist of the optional angular ridges or teeth-like features formed in the distal end 43 of the retainer configured to contact and engage the proximal end 52 of the tubular member 50. It will be appreciated by one skilled in the art that the retaining means may have various other configurations and perform the function thereof.

Specifically, as the retainer 40 is inserted into the hub 20, the distal end 43 of the retainer 40 contacts the flexible flared portion 53 of the proximal end 52 of the tubular member 50. In one embodiment in which the distal end 43 of the retainer 40, the teeth-like features resiliently contact the flared portion 53 of the proximal end 52 of the tubular member 50. As shown in FIG. 6, as the distal end 43 of the retainer 40 moves toward the distal end 23 of the hub 20, the flared portion 53 flexibly moves around the ridge 28 of the shoulder area 27 and the distal end 43 of the retainer 40 until both the distal end 43 of the retainer 40 and the proximal end 52 of the tubular member 50 are disposed in the groove 29. The cooperation between the distal end 43 of the retainer 40, the shoulder area 27 of the hub 20 and the proximal end 52 of the tubular member 50 forms a fluid tight seal. It will be appreciated by one skilled in the art that while in one embodiment, retainer 40 is resiliently engaged in lumen 24 of the hub 20 by a snap-fit or frictional engagement, various other methods of attachment could be utilized, such as welding, adhesives, mechanical fasteners and the like.

It will be appreciated that the proximal end 52 of the tubular member 50 may have various other configurations. The flared portion 53 may be generally conically shaped as depicted in FIG. 5. For example, the flared portion 53 at the proximal end 52 of the tubular member 50 may have various other shapes and configurations. In another embodiment, the flared portion 53 may be more cup-shaped. In addition in other alternative embodiments, flared portion 53, by way of example and not limitation, could be rounded or oval shaped, tapered, or any combination of the above-identified shapes. It will be appreciated that various other angles of the flare for flared portion 53 can be used as long as flared portion 53 is configured to cooperate with ridge 28 of shoulder area 27 and distal end 43 of retainer 40.

Figure 9:
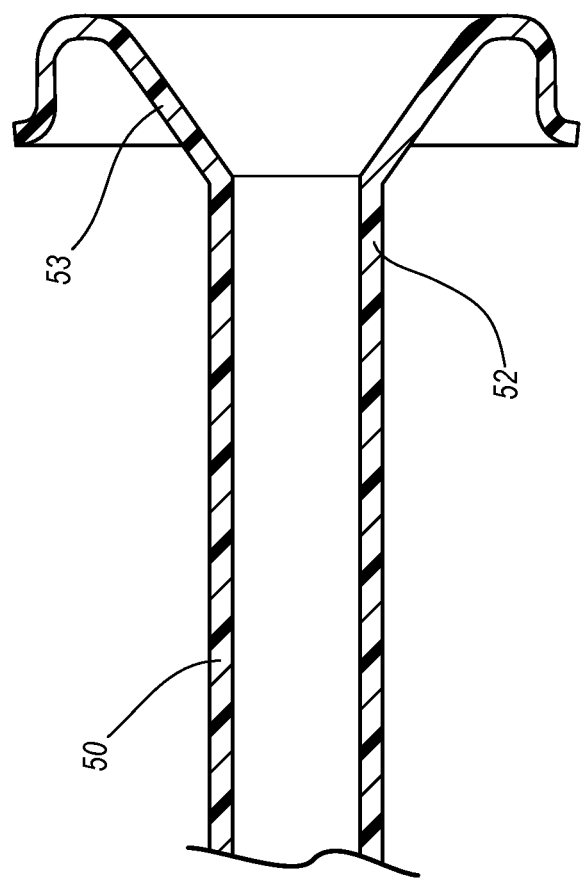
FIG. 9 is a partial cross-sectional view of an alternate embodiment of the flared portion of proximal end of an elongated tubular member of an introducer sheath in accordance with the present invention.

An alternate embodiment of the proximal end 52 of the tubular member 50 is illustrated in FIG. 9. In this embodiment, the proximal end 52 of the tubular member 50 is preformed to cooperate with the ridge 28 and groove 29 of the shoulder area 27 and the distal end 43 of the retainer 40. It will be appreciated that the ridge 28 and the groove 29 of the shoulder area 27 of the hub 20, the distal end 43 of the retainer 40, and the flared portion 53 of the distal end 52 of the tubular member 50 are another possible embodiment of a means for retaining tubular member 50 in the hub 20 in sealing engagement. It will be appreciated by one skilled in the art that the retaining means may have various other configurations and perform the function thereof.

It will be appreciated that, although it is not illustrated, the distal end 57 of the tubular member 50 can include a tapered portion depicted in FIG. 6 in which the diameter of the tubular member 50 is gradually reduced. Such a tapered portion may be produced through known manufacturing methods such as drawings, sanding, grinding, heat forming or other similar processes.

FIGS. 4 and 6 are partially exploded cross-sectional views of the introducer sheath 10 in accordance with the present invention during different phases of the assembly process. To assemble the individual components described above into a completed introducer sheath 10, the distal end (not shown) of the tubular member 50 is passed through the central lumen 24 of the hub 20 as depicted in FIG. 4. The flared portion 53 of the proximal end 52 of the tubular member 50 is received proximate to the shoulder area 27 of the main body 21 of the hub 20. More specifically, in one embodiment depicted in FIG. 4, the flared portion 53 of the proximal end 52 of the tubular member 50 cooperates with the ridge 28 of the shoulder area 27 in the hub 20.

Next, as previously mentioned and now illustrated in FIG. 6, the retainer 40 is disposed into the central lumen 24 of the main body 21 of the hub 20. As a result, the distal end 43 of the retainer 40 contacts the flared portion 53 of the proximal end 52 of the tubular member 50. In one embodiment of the present invention, the optional angular teeth-like features formed in the interior surface of distal end 43 of retainer 40 contact and resiliently engage the flared portion 53 of the proximal end 52 of the tubular member 50. As illustrated in FIG. 6, the flared portion 53 of the tubular member 50 and the ridge 28 are configured to cooperate such that the tubular member 50 is retained in the distal end of the hub 20.

As the retainer 40 continues to be moved distally, the locking features 41 of the retainer 40 are received by corresponding locking features 26 formed within the second lumen portion 24b of central lumen 24 of the hub 20, thereby locking the retainer 40 and the tubular member 50 to the hub 20. As the distal end 43 of the retainer 40 moves toward the distal end 23 of the hub 30 until the locking features 41 and 26 engage, the flared portion 53 of tubular member 50 flexibly moves around the ridge 28 of the shoulder area 27 formed in the interior body 21 of the hub 20. When the locking features 41 and 26 engage, the distal end 43 of the retainer 40 has moved the flared portion 53 of the proximal end 52 around the ridge 28 and into the groove 29 such that both the distal end 43 of the retainer 40 and the proximal end 52 of the tubular member 50 are disposed in the groove 29 as illustrated in FIG. 6.

The flexible membrane 60 is now inserted into the proximal end 22 of the main body 21 of the hub 20. In particular, the distal end 62 of the flexible membrane 60 is disposed in the recess 45 formed in the proximal end 42 of the retainer 40. Next, the cap 30 is likewise inserted into the proximal end 22 of the main body 21 of the hub 20. The proximal end 63 of the flexible member 60 is disposed into the recess 31 formed in the outer surface 32 of the cap 30. As illustrated in FIG. 2, the retainer 40, the cap 30, and the main body 21 of the hub 20 cooperate to hold the flexible member 60 in place.

In one embodiment, the flared portion 53 of the tubular member 50 can be utilized to align the lumen of the tubular member 50 with central lumen 24 of the main body 21 of hub 20 such that a single axis bisects the flexible membrane 60, the hub 20, the retainer 40, the cap 30, and the tubular member 50.

As shown in FIGS. 2, 4 and 6, the main body 21 of the hub 20 can also include an aperture 25, wherein the aperture 25 is configured to be in fluid communication with the lumen 44 of the retainer 40 and the lumen 59 of the elongated tubular member 50. Although not shown, a flexible piece of tubing with a luer fitting or a valve assembly can be attached to the aperture 25 so that fluid can pass through the valve/luer and flexible tubing into the lumen 44 of the retainer 40 and the lumen 59 of the tubular member 50.

Alternatively, a finger grip (not shown) may be substituted in place of the valve/luer fitting and tubing in the event that the introducer is to be utilized with a vessel closure system such as that shown in U.S. patent application Ser. No. 10/356,214 filed Aug. 5, 2004 entitled "Clip Applier and Methods of Use" the entirety of which is hereby incorporated by reference.

Introducer sheath 10 also includes optional strain relief member 80 illustrated in FIGS. 1 and 2. In one embodiment strain relief member 80 is generally cup shaped and configured to cooperate with distal end 23 of hub 20. Strain relief member 80 has a central opening formed therein which is configured to receive elongated tubular member 50 therein. It will be appreciated that the strain relief member 80 may have various other configurations and perform the function thereof as long as is cooperates with distal end 23 of hub 20. In an alternate embodiment, strain relief member 80 and hub 20 are a unitary piece. It will be appreciated that strain relief member 80 and hub 20 may be made from differing materials.

Figure 7:
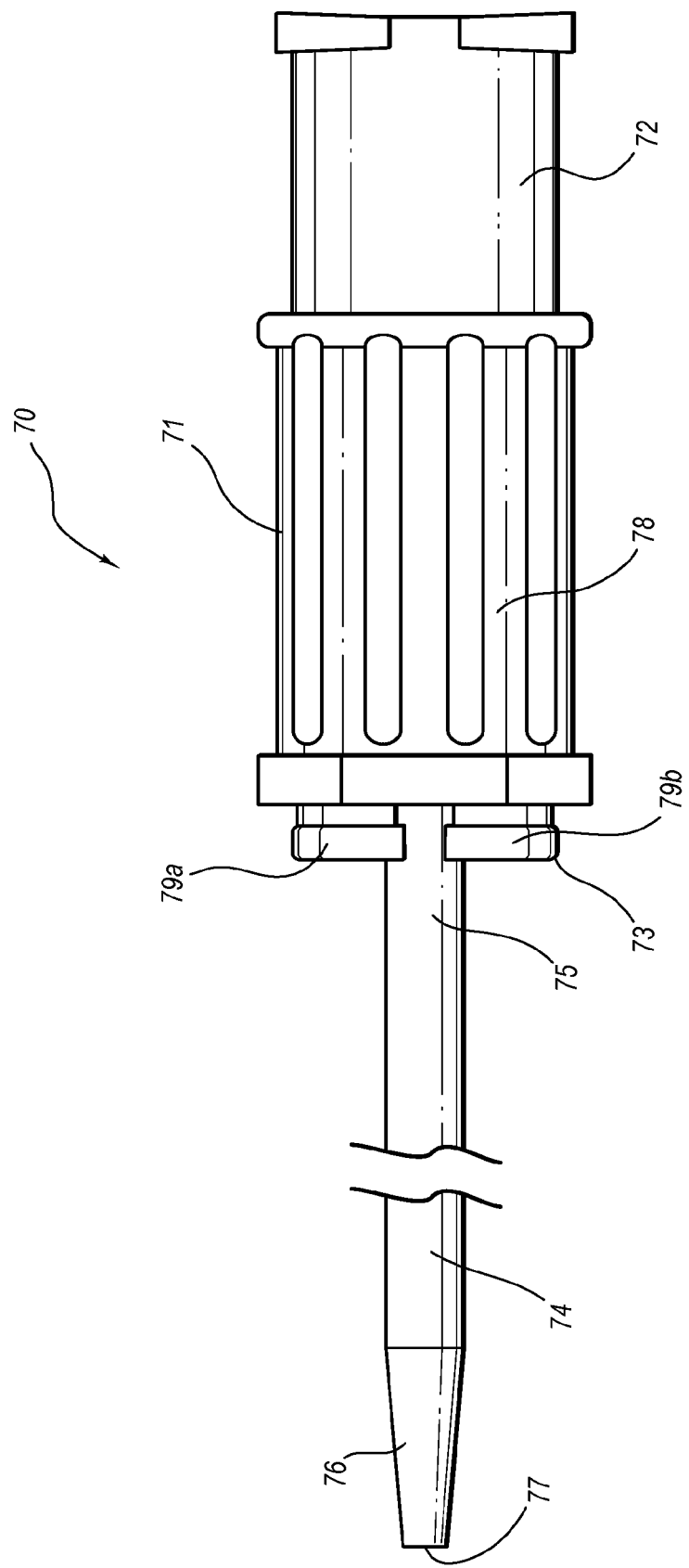
FIG. 7 is a partial elevation view of one exemplary embodiment of a dilator used with the introducer sheath of FIG. 2 in accordance with the present invention.

Referring now to FIG. 7, there is shown an exemplary embodiment of a dilator 70 that can be utilized in conjunction with the introducer sheath 10 of the present invention. The dilator 70 includes an elongated shaft member 74 having a proximal end 75 and a distal end 76. In one embodiment depicted in FIG. 7, the distal end 76 includes a tapered portion 77 configured for entering and expanding an opening in a vessel.

The dilator 70 also includes a handle 71 which has a proximal end 72 and a distal end 78. Distal end 78 of handle 71 is coupled to the proximal end 75 of the elongated shaft member 74. A resilient locking feature 73 is formed at the distal end 78 of the handle 71. As shown in FIG. 7, the locking feature 73 includes a first deflectable member 79a and a second deflectable member 79b which are configured to be received within the aperture 33 of the cap 30.

As illustrated in FIGS. 4 and 6, in one embodiment the aperture 33 of the cap 30 includes a ridge 34. When the resilient locking feature 73 of the handle 71 is disposed into the aperture 33, the first deflectable member 79a and the second deflectable member 79b resiliently deflect to pass over the ridge 34 until the first and second deflectable members 79a and 79b move back into position, thereby removably locking the handle 71 into place as illustrated in FIG. 9. The locking feature 73 of the dilator 70 is advantageous over conventional designs in that the first and second deflectable members allow for more consistent locking and release forces. In addition, the present invention increases the strength of the attachment between the cap 30 and the dilater 70. It will be appreciated that various other conventional methods for removably attaching the dilator 70 to cap 30 may be utilized. One skilled in the art would appreciate that this could include threaded engagements, and other types of mechanical attachments.

Figure 10:
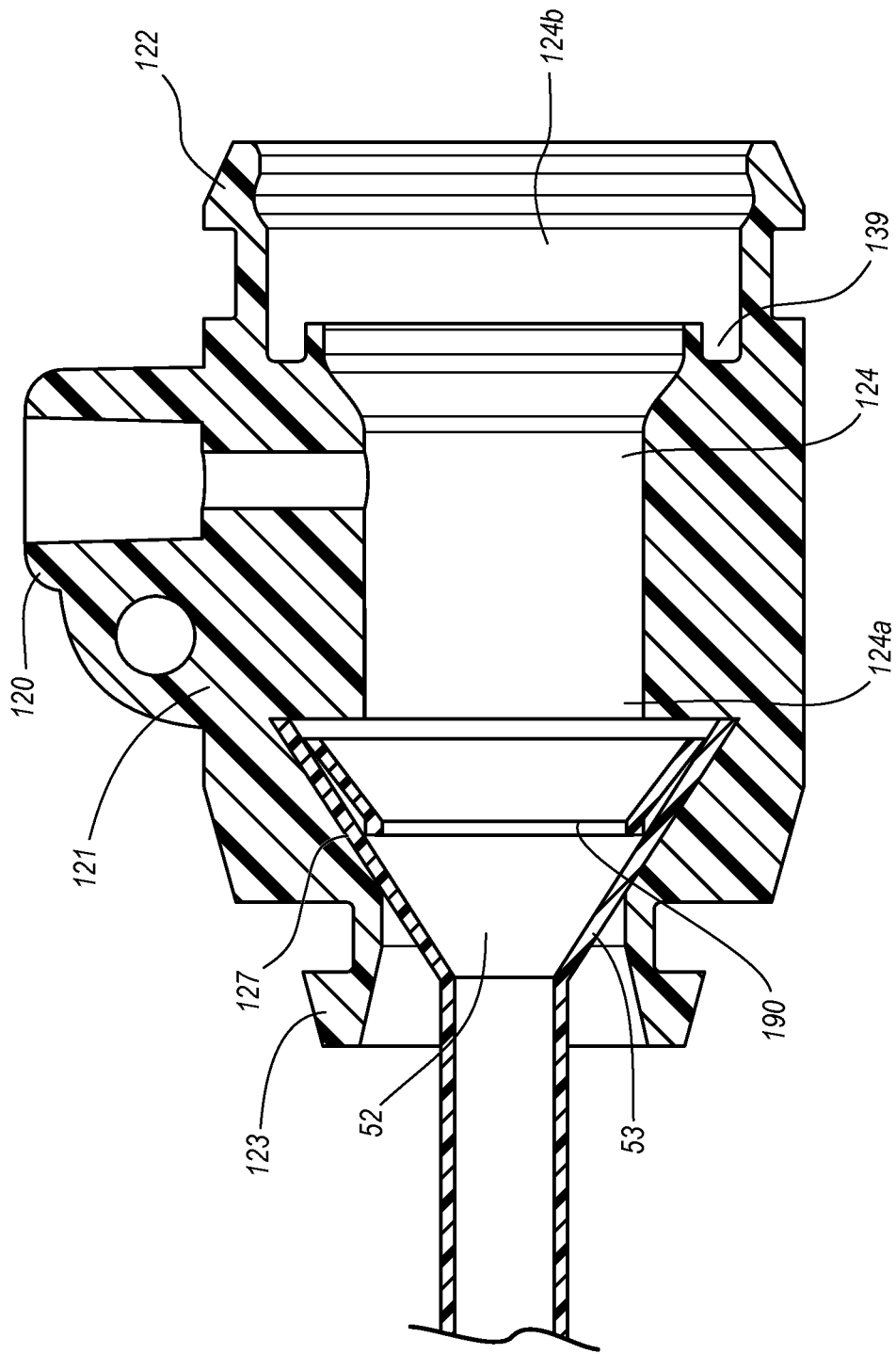
FIG. 10 is a partial cross-sectional view of an alternate embodiment of a portion of an overmolded introducer sheath in accordance with the present invention illustrating an overmolded hub, proximal end of the tubular member and a locking ring.

FIG. 10 depicts another embodiment of hub 120 in a different embodiment of an introducer sheath of the present invention. In this embodiment, the majority of the components of the introducer sheath 110 that were previously discussed are also compatible with the hub 120. Only the differences will be discussed in detail. The hub 120 includes a main body 121 having a proximal end 122 and a distal end 123 and a central lumen 124 extending therebetween. In this embodiment of the hub 120 depicted in FIG. 10, the central lumen 124 of the hub 120 comprises a first lumen portion 124a and a second lumen portion 124b. The first lumen portion 124a and the second lumen portion 124b have a common central axis. The first lumen portion 124a is proximate to the distal end 123 of the hub 120 while the second lumen portion 124b is proximate to the proximal end 122 of the hub 120. The second lumen portion 124b is sized and configured to receive the flexible membrane 60 and the cap 30 therein. This exemplary embodiment of the hub 120 has eliminated the need for a retainer such as retainer 40 illustrated in FIG. 4. In one embodiment, the first lumen portion 124a and the second lumen portion 124a are of differing size.

In the embodiment of the hub 120 depicted in FIG. 10, in this embodiment the introducer sheath includes a lock ring 190. FIG. 11a depicts one exemplary embodiment of a lock ring 190. Lock ring 190 has a distal portion 192 and a proximal portion 194. In one embodiment of the lock ring 190 illustrated, the distal portion 192 has a rounded outer peripheral shape. It will be appreciated that the distal portion 192 could have various other shapes as long as it is shaped and configured to cooperate with first lumen portion 124a. By way of example and not limitation, the shape of distal portion 192 of lock ring 190 could be oval, elliptical or various combinations thereof. The distal portion 194 of the lock ring 190 is configured to cooperate with flared portion 53 of proximal end 52 of tubular member 50. In an exemplary embodiment, the proximal portion 194 of lock ring 190 is flared as illustrated.

In the exemplary embodiment, of the lock ring 190 illustrated in FIG. 11a, the lock ring 190 includes posts 196 which are formed on the exterior surface of the lock ring 190. In one embodiment, posts 196 extend along the outer surface of the lock ring 190 and in this embodiment are substantially parallel to the central axis of the introducer sheath. In the exemplary embodiment depicted in FIG. 11a, the posts 196 extend on the outer surface of the distal portion 192 of lock ring 190 and along the proximal portion 194 until the angle of the flare intersects them. It will be appreciated that the posts 196 could have differing sizes and lengths. In exemplary embodiment illustrated in FIG. 11a, the lock ring 190 has four posts 196 which are equally spaced along the exterior surface of the lock ring. It will be appreciated that differing numbers of posts 196 as well as different spacing of the posts 196 could be utilized.

Figure 11B:
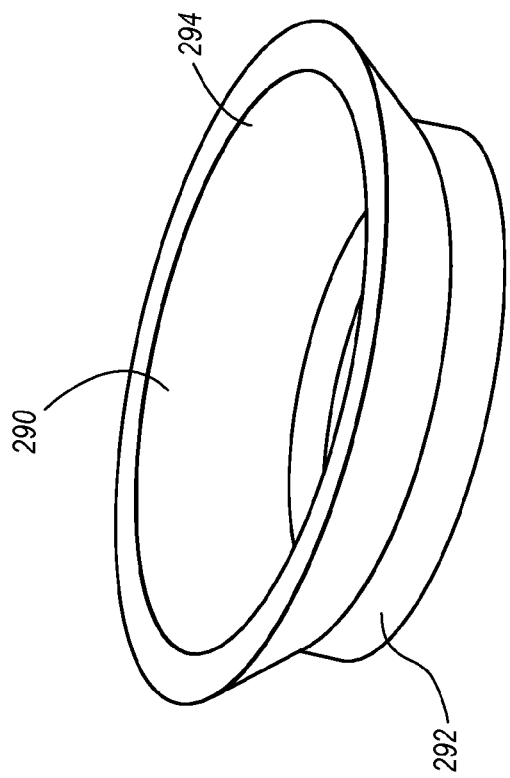
FIG. 11b is a perspective view of an alternate embodiment of a locking ring used in the introducer sheath of FIG. 10.
Figure 11A:
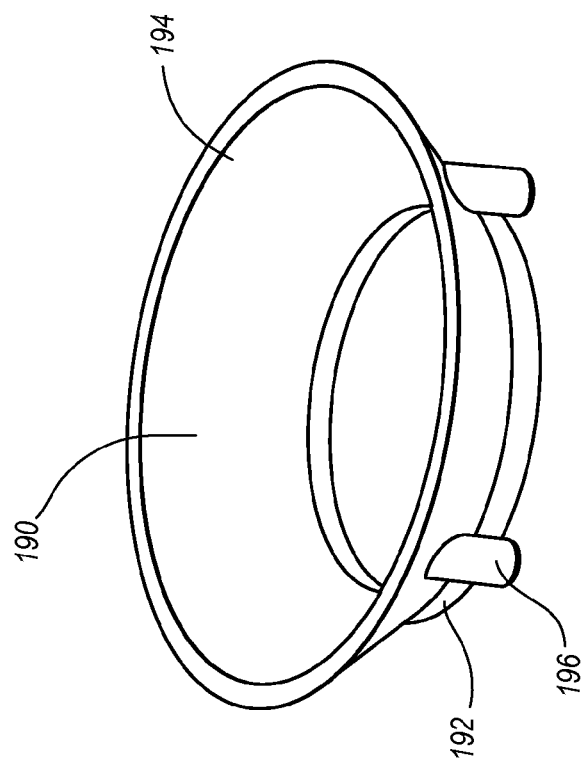
FIG. 11a is a perspective view of one embodiment of a locking ring used in the introducer sheath of FIG. 10.

FIG. 11b illustrates another embodiment of a lock ring 290 for use in an introducer sheath of the present invention. In this embodiment, lock ring 290 has a distal portion 192 and a flared proximal portion 194 but does not include the posts 196.

With the embodiment of introducer sheath which uses a lock ring and eliminates the need for a retainer, the hub 120 is formed using a conventional overmolded platform in which the flared portion 53 of proximal end 52 of tubular member 50 and lock ring 190 are positioned and hub 120 is molded around them. In one embodiment, the angle of the flare of the flared portion 53 is about 30 to about 35 degrees from the central axis. It will be appreciated that various other angles of the flare for flared portion 53 can be used as long as flared portion 53 is configured to cooperate with lock ring 190 and shoulder area 127. Once molded, the lock ring 190, the flared portion 53 of proximal end 52 of tubular member 50, and hub 120 form a fluid tight seal.

In the embodiment illustrated in FIG. 10, the distal end 57 of the tubular member 50 extends outwardly from hub 120. The flared portion 53 of the proximal end 52 of the tubular member 50 is proximate to the shoulder area 127 of the main body 21 of the hub 120. In an exemplary embodiment of the present invention, the beginning of flared portion 53 is located generally proximate to the distal end 123 of the hub 120. It will be appreciated that various lengths of flared portion 53 and locations of the beginning of flared portion 53 can be utilized and still perform the function thereof.

The distal portion 192 of the lock ring 190 cooperates with the flared portion 53 of proximal end 52 of tubular member 50. In this embodiment, the proximal end 122 of the hub 120 is configured to cooperate with the distal end 62 of flexible membrane 60. In this exemplary embodiment of the hub 120, the second lumen portion 124b is configured to receive flexible membrane 60 therein. As illustrated in FIG. 10, the hub 120 has a channel 139 formed therein which is configured to receive the distal end 60 of flexible membrane 60 therein. The remainder of the assembly of the introducer sheath is consistent with that previously discussed.

In accordance with the present invention, an introducer sheath or components thereof can be formed using one or more materials. Typically, the materials used in forming the introducer sheath are medical grade synthetic materials or plastics. Exemplary materials may include, but are not limited to, flexible PVC, polyurethane, silicone, liner low-density polyethylene ("LLDPE"), polyethylene, high density polyethylene, ("DHPE"), polyethylene-lined ethylvinyl acetate ("PE-EVA"), polypropylene, latex, thermoplastic rubber, polytetrafluoroethylene (PTFE), expandable polytetrafluoroethylene (ePTFE), fluoroethylene-propylene (FEP), perfluoroalkoxy (PFA), ethylene-tetrafluoroethylene-copolymer (ETFE), ethylene-chlorotrifluoroethylene (ECTFE), polychloro-trifluoroethylene (PCTFE), polyimide (PI), polyetherimide (PEI), polyetherketone (PEEK), polyamide-imide (PAI), other fluoropolymers, and the like.

Exemplary materials used in the introducer sheath or the components of the sheath can also include elastomers or thermoplastic elastomers. Examples of elastomers include, but are not limited to, natural rubber, silicone rubber, polyurethane rubber, polybutadiene, polyisoprene, chlorosulfonated polyethylene, polysulfide rubber, epichlorohydrin rubber, ethylene propylene rubber, and the like or any combination thereof. These materials provide the elasticity that enable the sheath to expand and/or contract to accommodate the removal/insertion of a medical device as required. Other materials that can be used can include, but are not limited to, dip coated type silicones.

In other embodiments, the materials suitable for use in an introducer sheath and the components thereof are configured to have chemical resistance, crack resistance, no toxicity, Food and Drug Administration ("FDA") compliance, non-electrically conductive, dimensional stability, and/or be sterilized by ethylene oxide, gamma radiation, autoclave, UV light, ozone, and the like.

In addition, the selection of materials for a particular introducer sheath or its components can depend on a variety of factors that include, but are not limited to, a particular stiffness and/or flexibility of the sheath or any portion of the sheath, including the desired column stiffness and strength to enable insertion of the sheath, a particular shear or split strength for the sheath or any portion of the sheath, the ability to resist kinking, and the like. For example, the material used for the tubular portion of the introducer sheath may be selected based on shear strength or how easily it can be split. Further, certain features of the sheath may be formed to enhance certain characteristics. For example, a strain relief portion may be formed so as to resist kinking while the elongated tubular portion may be formed to facilitate splitting.

When more than one material is used to form the sheath or to form specific portions of the introducer sheath, the materials may be selected, in addition to the factors identified herein, on a bond strength between the materials or on the elasticity of a particular material. The bond strength, for example, may have an impact on the splitability of the sheath or of a portion of the sheath. The bond strength may also affect the ability of the sheath to expand without splitting.

When an elastomer is used in the sheath or a component of the sheath, the elasticity of the elastomer enables the sheath or a portion of the sheath to at least partially deform, resiliently deform, or elastically expand as needed to accommodate a medical device and then return or substantially return to its configuration prior to deforming or expanding. Advantageously, the ability to deform and/or expand permits a device, such as an expanded or expandable balloon, to be withdrawn through the sheath without removing the sheath, for example from a patient's vasculature. This maintains access to the patient's vasculature without the difficulty of inserting another sheath or medical device through the puncture site. Further, maintaining the introducer sheath in place allows a physician or technician to insert one or more additional medical devices, such as a vessel closure device, using the introducer sheath. It will be appreciated that the introducer sheath will be used in a variety of medical procedures.

For example, the introducer sheaths disclosed herein are intended to be utilized in combination with a vessel closure device such as those shown in U.S. Pat. No. 6,197,042 and pending U.S. patent application Ser. No. 10/356,214, filed Aug. 8, 2004 entitled "Clip Applier and Methods of Use", which are both assigned to a common owner and are hereby incorporated by reference herein in their entireties.

In one embodiment, the hub 20, the retainer, and the cap, may be constructed of materials such as acrylonitrile butadiene styrene (ABS), polyvinylchloride (PVC), polycarbonate. In one embodiment, the hub 20 is formed through injection molding. Any of the materials may further include glass reinforcement particles mixed therewith.

In an exemplary embodiment, the elongated tubular member 50 is constructed of polytetrafluoroethylene, Teflon, and similar materials. In one embodiment the tubular member 50 is generally fabricated through extrusion. The tubular member 50 as described herein may be constructed of a single material or may be constructed of more than one material. For example, the tubular member 50 may be constructed of two or more materials by utilizing a co-extrusion process.

It will be appreciated by one skilled in the art, that various other materials can be used for these individual components. For example, any of the above identified materials may further include glass reinforcement particles mixed therewith. Further, various other methods of manufacture could be utilized.

Further still, it is contemplated that a geometric feature may be formed within the wall of the tubular member 50. An example of such feature is a sinusoidal pattern formed within the wall of the tubular member 50. The sinusoidal pattern may be beneficial in that it may promote easier splitting of the sheath if desired. Additionally, an introducer sheath having this type of pattern may also reduce friction between the sheath and medical devices disposed through the sheath as the medical device will only contact the sheath at various points along the length of the sheath versus contacting the wall of the sheath along the entire length of the sheath.

Figure 14:
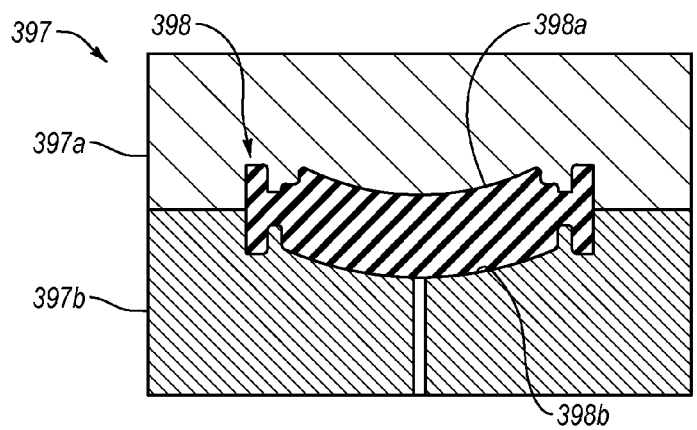
FIG. 14 illustrates an embodiment of a mold for manufacturing the flexible valve member of FIG. 12.
Figure 16:
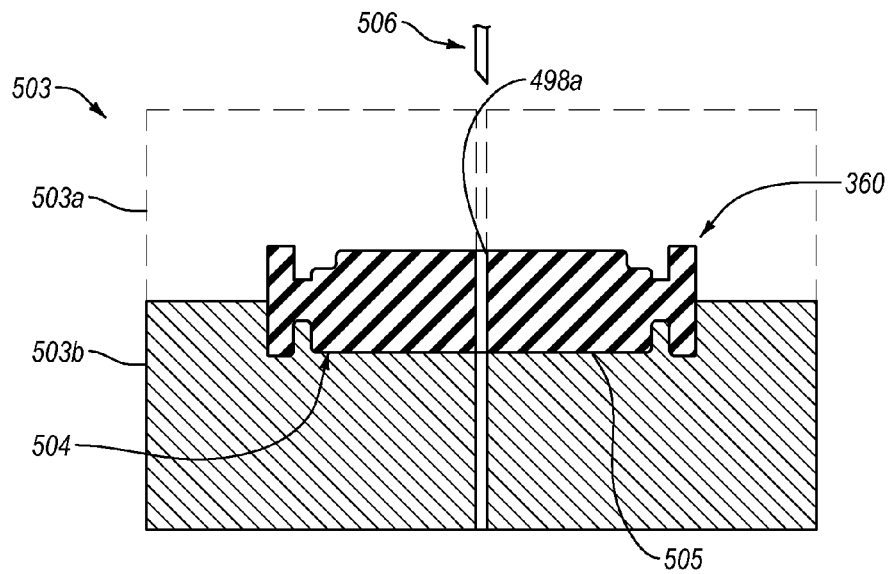
FIG. 16 illustrates an embodiment of a cutting assembly.

Referring generally to FIGS. 12, 14, 16, and 19-20, FIG. 12 illustrates a further embodiment of a flexible membrane or hemostasis valve 360; FIG. 14 illustrates an embodiment of a mold 397 for manufacturing the flexible valve member 360 of FIG. 12; FIG. 16 illustrates an embodiment of a cutting assembly 506; FIGS. 19 and 19A illustrate a further embodiment of an introducer sheath 310 with a medical device 2 inserted through the flexible valve member 360 of FIG. 12; and FIGS. 20 and 20A illustrate the embodiment of the introducer sheath 310 of FIG. 19 with a medical device 2 inserted through the flexible valve member 360 of FIG. 12 and retracted to a retracted state. FIGS. 19A and 20A are enlargements about sections 19A, 20A, respectively, showing a closer view of the flexible valve member 360 of FIG. 19 in the compressed and retracted states, respectively.

The introducer sheath 310 and/or components thereof may be at least partially functionally similar to that of the introducer sheaths 10, 110 or components thereof previously described herein in most respects, wherein certain features will not be described in relation to this embodiment wherein those components may function in the manner as described above and are hereby incorporated into this alternative embodiment described below. Similarly, at least some aspects of introducer sheath 310 may be incorporated into other introducer sheaths described herein. Like structures and/or components are given like reference numerals. For example, the arrangement of the hub 320 and tubular member 350 may be incorporated into the other introducer sheaths described herein. Like structures and/or components are given like reference numerals.

As shown in FIGS. 19-20, the hub 320, the retainer (shown as 40 in FIG. 4), and the tubular member 350 may be integrally formed. In the present embodiment, the hub 320 and retainer (not shown) may be formed together and then be overmolded over the tubular member 350. In other embodiments, the hub 320, retainer, and tubular member 350 may be formed together. For example, the introducer sheath 310 may be formed according to the process described in connection with FIGS. 10 and 11A and 11B.

The introducer sheath 310 may include a shoulder area 327. The shoulder area 327 may be overmolded over a corresponding shelf portion 354 extending from a flared portion 353 of the introducer sheath 310 and/or a lock ring 390 may be used to retain the tubular member 350.

In the present embodiment, the introducer sheath 310, as shown in FIG. 19, may exclude a port (such as port 25 shown in FIGS. 3 and 6). In other embodiments, the introducer sheath 310 may include a port.

The flexible valve member 360 may be at least partially functionally similar to that of the flexible valve member 60 previously described above and shown in FIGS. 1-2, 4, 6, and 8 in most respects, wherein certain features will not be described in relation to this embodiment wherein those components may function in the manner as described above and are hereby incorporated into this alternative embodiment described below. Similarly, at least some aspects of flexible valve member 360 may be incorporated into other flexible valve members described herein. Like structures and/or components are given like reference numerals.

The flexible membrane 360 includes an opening and/or a plurality of slits formed therein to form an opening 361. The opening 361 allows a medical device (shown as 2 in FIGS. 19-20) to pass through the flexible membrane 360. It will be appreciated that the opening 361 of the flexible membrane 360 may have various other configurations and perform the functions thereof. The flexible membrane 360 and the opening 361 are sized and configured to form a fluid tight seal about the medical device.

Figure 16A:
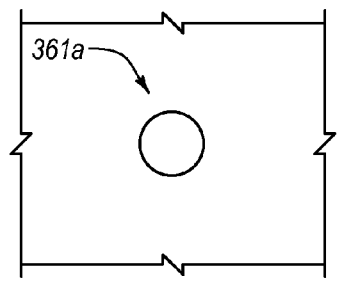
FIGS. 16A-16B illustrate two embodiments of openings that may be formed in a flexible valve member.
Figure 16B:
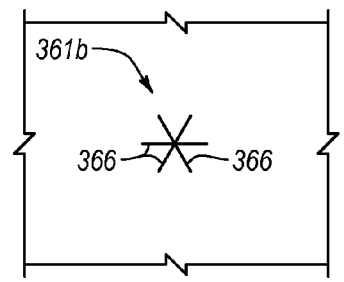

FIGS. 16A-16B illustrate two embodiments of openings 361 that may be formed in the flexible valve member 360. FIG. 16A illustrates a substantially cylindrical opening 361a that may be formed in the flexible valve member 360. The opening 361a may be formed by means of a cutting tool (such as cutting tool 506 shown in FIG. 16), such as a rotating drill, punch, actuated blade, or the like. FIG. 16B illustrates another opening 361b. The opening 361b may include at least one slit 366. In the present embodiment, the opening 361b is formed from three slits 366. More and/or fewer slits 366 may be used to form the opening 361b. The opening 361b may be formed by means of a cutting tool (such as cutting tool 506 shown in FIG. 16), such as a rotating drill, punch, actuated blade, or the like. In the present embodiment, the opening 361b may be formed by inserting a razor blade through the flexible valve member to form each slit 366.

As shown in FIG. 19, the flexible valve member 360 may be configured to cooperate with the proximal end 342 of the hub 320. In other embodiments, the flexible membrane 360 may be configured to cooperate with a retainer (such as retainer 40 shown in FIG. 4) or other compound of the introducer sheath 310. More specifically, for example, the distal end 362 of the flexible membrane 360 may be received by a recess 345 formed in the proximal end 342 of the hub 320. The distal end 362 of the flexible membrane 360 may include an opening 364 formed therein configured to cooperate with the proximal end 342 of the hub 320.

In the embodiment shown in FIG. 19, a cap 330 may be configured to cooperate with the proximal end 363 of the flexible membrane 360. In particular, in this embodiment, the exterior surface of the cap 330 may include a recess 331 formed therein which may be configured to receive the proximal end 363 of the flexible membrane 360. Similarly, the proximal end 363 of the flexible member 360 may include an opening 365 formed therein that may be configured to receive a portion, such as distal portion 336, of the cap 330.

It will be appreciated that a distal portion 336 of the cap 330 and the opening 365 in the proximal end 363 of the flexible membrane 360 may have various other configurations and shapes as long as they are configured to cooperate and/or have a sealing engagement. It will be appreciated that a recess 331 of the cap 330 could have various other configurations as long as the proximal end 363 of the flexible membrane 360 and the recess 331 are correspondingly shaped to cooperate.

In some embodiments, the orientation of the flexible valve member 360 in a relaxed state, a compressed state, a retracted state, or combinations thereof may be determined by the relationship between the distal end 335 of the cap 330 and the proximal end 342 of the hub 320. As shown in FIGS. 19-20, the cap 330 may include a proximal engaging surface 337 and the hub 320 may include a distal engaging surface 347. For example, the recess 331 and an aperture 333 of the cap 330 may form the proximal engaging surface 337 and the recess 345 and a lumen 344 of the hub 320 may form the distal engaging surface 347. As shown in FIG. 19, the flexible membrane 360 is seated within the introducer sheath 310 with the distal end 362 extending distally and in phantom with the proximal end 363 extending proximally.

In some embodiments, the position of the proximal engaging surface 337 and the distal engaging surface 347 with respect to each other may determine the orientation of the flexible valve member 360. In the present embodiment, the flexible valve member 360 may be in a substantially non-planar (i.e. not parallel to a lateral plane, such as a flat plane perpendicular to and through the longitudinal axis of the introducer sheath 310, and/or not flat, for example, convex or concave) configuration in a relaxed state and in a compressed state, regardless of the relationship between the distal end 335 of the cap 330 and the proximal end 342 of the hub 320. However, the relationship between the distal end 335 and the proximal end 342 may affect the degree of non-planarity of the flexible member 360 in the compressed state.

In the present embodiment, the proximal engaging surface 337 and the distal engaging surface 347 may have substantially the same surface area and/or may be oriented to mate with each other. For example, without the valve member 360, the proximal engaging surface 337 and distal engaging surface 347 would substantially overlap each other when assembled. In another example, the proximal engaging surface 337 and distal engaging surface 347 may be circumferentially aligned. The proximal engaging surface 337 may include an outer edge 338 and/or an inner edge 339. The distal engaging surface 347 may include an outer edge 348 and/or an inner edge 349.

Circumferential alignment may include the circumferential alignment of the outer edge 338 of the proximal engaging surface 337 with the outer edge 348 of the distal engaging surface 347 and/or the circumferential alignment of the inner edge 339 of the proximal engaging surface 337 with the inner edge 349 of the distal engaging surface 347. For example, as shown in FIG. 19, the outer edge 338 of the proximal engaging surface 337 is circumferentially aligned (i.e. coplanar and/or parallel in this example) with the outer edge 348 of the distal engaging surface 347 and the inner edge 339 of the proximal engaging surface 337 is circumferentially aligned (i.e. coplanar and/or parallel) with the inner edge 349 of the distal engaging surface 347. In another example, the outer edge 338 of the proximal engaging surface 337 may have an axial dimension (i.e. diameter) that is the same as an axial dimension of the outer edge 348 of the distal engaging surface 347 and/or the inner edge 339. As an axial dimension of the inner edge 349. In other embodiments, the proximal engaging surface 337 and distal engaging surface 347 may be oriented such that they only partially overlap and/or do not overlap at all.

Figure 12:
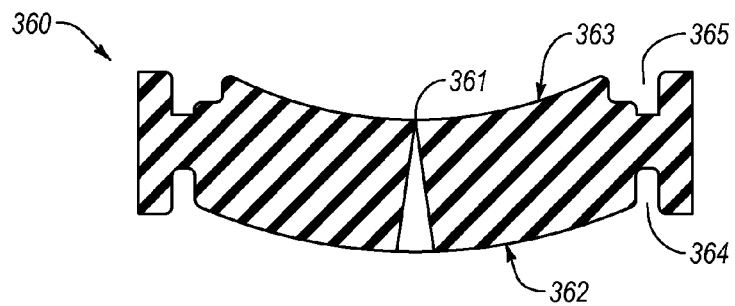
FIG. 12 illustrates a further embodiment of a flexible membrane or hemostasis valve.

As shown in FIG. 12, the distal end 362 and proximal end 363 are substantially coplanar (i.e. a first curved plane defined through the outer surface of the distal end 362 and a second curved plane defined through the outer surface of the proximal end 363 would not intersect) and/or non-planar (i.e. not parallel to a lateral plane, such as a flat plane perpendicular to and through the longitudinal axis of the introducer sheath 310, and/or not flat, for example, convex or concave) while in a relaxed state (i.e. not inserted into the introducer sheath 310). As shown in FIG. 19, the distal end 362 and proximal end 363 are substantially coplanar and/or non-planar while in a compressed state (i.e. inserted into the sheath 310). Specifically, the distal end 362 and proximal end 363 may not intersect and/or may be convex or concave.

The opening 361 may have a varying cross-sectional dimension, such as the inner diameter, in the relaxed state. For example, as shown in FIG. 12, the opening 361 is substantially conical rather than cylindrical. As shown in FIG. 20, the distal end 362 and proximal end 363 may be substantially coplanar and/or planar while in a retracted state (i.e. when inserted into the sheath 310 but retracted proximally by a medical device 2). The opening 361 may have a substantially constant cross-sectional dimension, such as the inner diameter, in the retracted state.

Although the opening 361 is shown as substantially conical, in FIG. 12, the opening 361 may have varying shapes. For example, for larger compressive stresses (or forces) on the distal end 362 or proximal end 363, the inner surfaces (not shown) of the opening 361 may be substantially abutting in the relaxed state near the end (i.e. distal end 362 or proximal end 363) with the larger compressive stresses (or forces). In embodiments where the compressive stresses (or forces) are induced in (or applied to) both the distal end and proximal end (such as distal end 62 and proximal end 63 shown in FIG. 4), whether those stresses (or forces) are induced in (or applied to) the distal end and proximal end through the molding processes (as in the flexible valve member 360) or through compression in the sheath, the inner surfaces of the opening 361 may be touching in the relaxed, compressed, retracted, other states, or combinations thereof.

The circumferential alignment of the proximal engaging surface 337 and the distal engaging surface 347 may affect the forces (or stresses) applied to (or induced in) the flexible valve member 360. For example, the compressive force exerted on (or induced in) the flexible membrane 360 may be an axial compressive force (or stress) that may cause the opening 361 to be squeezed and thereby forming a more fluid tight seal therein. As shown in FIG. 2, the compressive forces (or stresses) may be generally applied to (or induced in) both the proximal end 363 and the distal end 362 of the flexible valve member 360. As shown in FIG. 19, a compressive stress (or force) may be generally induced in (or applied to) the proximal end 363 of the flexible valve member 360 while a tensile and/or axial stress (or force) may be generally induced in (or applied to) the distal end 362 of the flexible valve member 360.

In other embodiments, the stresses (or forces) may be induced in (or applied to) only the proximal end 363 or the distal end 362, the stresses (or forces) may be unevenly induced in (or applied to) the proximal end 363 and/or the distal end 362, other stresses (or forces) may be induced in (or applied to) the proximal end 363 and/or the distal end 362, or combinations thereof.

Referring to FIG. 14, the flexible valve member 360 may be formed within a mold 397. As is apparent in FIG. 14, the mold 397 includes mold portions 397a, 397b combinable to form a cavity 398 that may be filled with a liquid polymer that becomes solid through a cooling or curing process. The cavity 398 may include surfaces 398a, 398b positioned on the distal end 362 and/or the proximal end 363 of the flexible valve member 360. The surfaces 398a, 398b may be shaped such that the distal end 362 and/or the proximal end 363 have an inverted or concave shape following the molding process as shown by the flexible valve member 360 shown in FIG. 12. For example, the surfaces 398a, 398b may have a spherical shape. Alternatively, the surfaces 398a, 398b may have a conical shape such that the distal end 362 and/or the proximal end 363 have a conical shape. Additional information regarding forming a non-planar valve may be found in related U.S. patent application Ser. No. 12/695,961, filed Jan. 28, 2010, which is incorporated herein by reference in its entirety.

Referring to FIG. 16, the concavity of the distal end 362 and/or the proximal end 363 may be reduced by deforming the distal end 362 and/or the proximal end 363 prior to forming the flexible valve member 360. In the illustrated embodiment, reduction of the concavity of the proximal end 363 is accomplished by inserting the flexible valve member 360 into a mandrel 503. The mandrel 503 may include an upper portion 503a (shown in phantom) and a lower portion 503b that define a cavity 504 around the distal end 362 and/or the proximal end 363. The mandrel 503 may have a base surface 505 that is flat or has a radius of curvature greater than an undeformed radius of curvature of the distal end 362 of the flexible valve member 360, such that as the mandrel 503 is urged against the distal end 362, the concavity of the distal end 362 and/or the proximal end 363 is reduced.

In the present embodiment, the upper portion 503a and lower portion 503b may be used to reduce the concavity of the flexible valve member 360. In other embodiments only the upper portion 503a or lower portion 503b may be used.

The opening 361 for the flexible valve member 360 may then be formed in the proximal end 363, such as by means of cutting tool 506, such as a rotating drill, punch, actuated blade, or the like. In other embodiments, the opening 361 may be molded into the flexible valve member 360. In embodiments, where the opening 361 is molded into the flexible valve member 360, additional stresses (or forces) may need to be induced in (or applied to) the flexible valve member 360 to maintain hemostasis in the compressed state. The mandrel 503 may then be removed to yield a flexible valve member 360 such as is illustrated in FIG. 12. In the present embodiment, the mandrel 503 substantially receives the distal end 362 and/or proximal end 363 of the flexible valve member 360. In some embodiments, the mandrel 503 may be configured to reduce the concavity of the distal end 362 and/or proximal end 363 of the flexible valve member 360 without substantially receiving the distal end 362 and/or proximal end 363 of the flexible member 360. For example, the mandrel 503 may be embodied by a rod (not shown) pressed against the distal end 362 and/or the proximal end 363 during the cutting step illustrated in FIG. 16. For example, the rod may have an upper surface that has an area substantially smaller than the area of the distal end 362 and/or the proximal end 363. For example, the rod may have an area that is slightly greater or smaller (i.e. ±5 to 10%) that of the opening 361.

Upon removal of the mandrel 503, the distal end 362 and/or the proximal end 363 may elastically return to its undeformed shape, causing the opening 361 to become tapered due to the return of the proximal end 363 to a concave shape. Although the mandrel 503 is discussed in connection with flexible valve member 360 of FIG. 12, the mandrel 503 may be used with any of the flexible valve members described herein, such as, but not limited to flexible valve members 60, 460, 660, 760.

Figure 13:
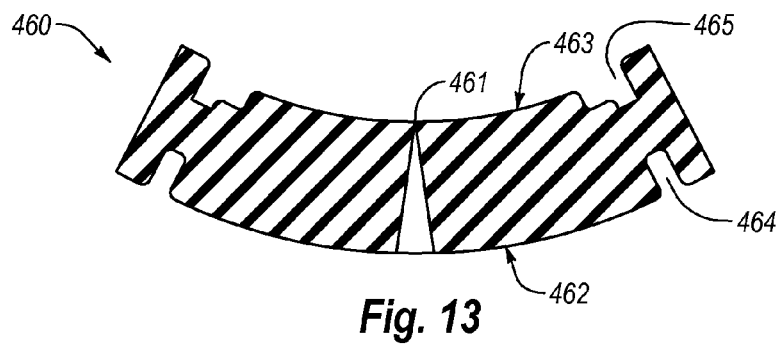
FIG. 13 illustrates a still further embodiment of a flexible membrane or hemostasis valve.
Figure 15:
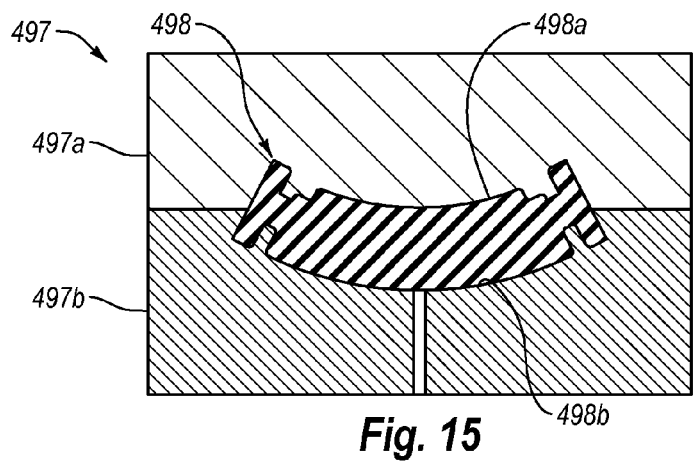
FIG. 15 illustrates a further embodiment of a mold for manufacturing the flexible valve member of FIG. 13.

Referring generally to FIGS. 13 and 15, FIG. 13 illustrates a further embodiment of a flexible membrane or hemostasis valve 460 and FIG. 15 illustrates an embodiment of a mold 497 for manufacturing the flexible valve member 460 of FIG. 13.

The flexible valve member 460 may be at least partially functionally similar to that of the flexible valve members 60, 360 previously described herein in most respects, wherein certain features will not be described in relation to this embodiment wherein those components may function in the manner as described above and are hereby incorporated into this alternative embodiment described below. Similarly, at least some aspects of flexible valve member 460 may be incorporated into other flexible valve members described herein. Like structures and/or components are given like reference numerals.

In the embodiment of a flexible valve member 360 shown in FIG. 12, the openings 364, 365 are generally vertically aligned with the opening 361, such that when they are inserted into the introducer sheath 310, the proximal engaging surface 337 of the cap 330 and the distal engaging surface 347 of the hub 320 engage the openings 364, 365 without substantially axially deforming the openings 364, 365.

As shown in FIG. 13, the openings 464, 465 of the flexible valve member 460 are generally vertically aligned with respect to each other, but are oriented at an angle with respect to the opening 461. When the flexible valve member 460 is inserted into introducer sheath 310, shown in FIGS. 19-20, the proximal engaging surface 337 of the cap 330 and the distal engaging surface 347 of the hub 320 engage the openings 464, 465. However, the flexible valve member 460 may be deformed when the openings 464, 465 are engaged by the cap 330 and hub 320.

This deformation may provide (or induce) a compressive force (or stress) to the flexible membrane 460, wherein the compressive force (or stress) exerted on (or induced) in the flexible membrane 460 causes the opening 461 to be squeezed and thereby forming a more fluid tight seal therein. This compressive force (or stress) however may not reduce access to or increase forces to pass a medical device through the opening 461 of the flexible membrane 460. Additionally, as described above, the compressive force (or stress) exerted on (or induced in) the flexible membrane 460 may increase the sealing of the opening 461 in a static state, the compressive force (or stress) may also increases the seal between the flexible membrane 461 and a medical device (such as medical device 2 shown in FIGS. 19-22) disposed through the opening 461 for the same reasons.

The circumferential alignment of a distal engaging surface and a proximal engaging surface (such as proximal engaging surface 337 and distal engaging surface 347 shown in FIGS. 19-20) may affect the forces (or stresses) applied to (or induced in) the flexible valve member 460. For example, the compressive force exerted on (or induced in) the flexible membrane 460 may be an axial compressive force (or stress) that may cause the opening 461 to be squeezed and thereby forming a more fluid tight seal therein. A compressive and/or axial stress (or force) may be generally induced in (or applied to) the proximal end 463 of the flexible valve member 460 while a tensile and/or axial stress (or force) may be generally induced in (or applied to) the distal end 462 of the flexible valve member 460.

In other embodiments, the stresses (or forces) may be induced in (or applied to) only the proximal end 463 or the distal end 462, the stresses (or forces) may be unevenly induced in (or applied to) the proximal end 463 and/or the distal end 462, other stresses (or forces) may be induced in (or applied to) the proximal end 463 and/or the distal end 462, or combinations thereof.

Referring to FIG. 15, the flexible valve member 460 may be formed within a mold 497. As is apparent in FIG. 15, the mold 497 includes mold portions 497a, 497b combinable to form a cavity 498 that may be filled with a liquid polymer that becomes solid through a cooling or curing process. The cavity 498 may include surfaces 498a, 498b positioned on the distal end 462 and/or the proximal end 463 of the flexible valve member 460. The surfaces 498a, 498b may be shaped such that the distal end 462 and/or the proximal end 463 have an inverted or concave shape following the molding process as shown by the flexible valve member 460 shown in FIG. 13. For example, the surfaces 498a, 498b may have a spherical shape. Alternatively, the surfaces 498a, 498b may have a conical shape such that the distal end 462 and/or the proximal end 463 have a conical shape. Additional information regarding forming a non-planar valve may be found in related U.S. patent application Ser. No. 12/695,961, filed Jan. 28, 2010, which is incorporated herein by reference in its entirety.

Figure 17:
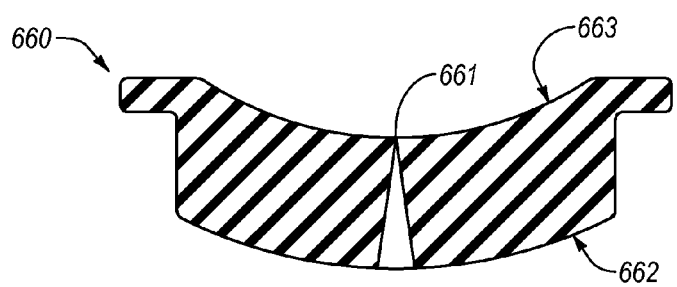
FIG. 17 is a yet further embodiment of a flexible valve member.
Figure 18:
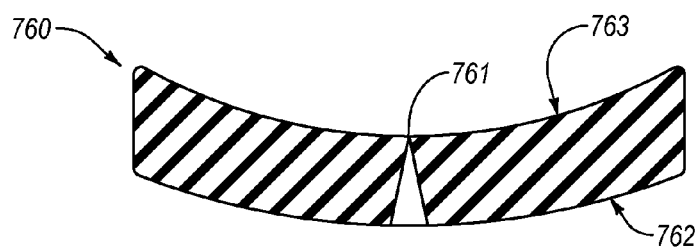
FIG. 18 is a still further embodiment of a flexible valve member.

Referring generally to FIGS. 17 and 18, FIG. 17 is a further embodiment of a flexible valve member 660 having a distal opening 664 but no proximal opening and FIG. 18 is a still further embodiment of a flexible valve member 760 without a proximal opening or a distal opening.

The flexible valve members 660, 760 may be at least partially functionally similar to that of the flexible valve members 60, 360, 460 previously described herein in most respects, wherein certain features will not be described in relation to these embodiments wherein those components may function in the manner as described above and are hereby incorporated into these alternative embodiments described below. Similarly, at least some aspects of flexible valve members 660, 760 may be incorporated into other flexible valve members described herein. Like structures and/or components are given like reference numerals.

Referring to FIG. 17, the flexible valve member 660 may be formed in a manner similar to the flexible valve members 360, 460. For example, the flexible valve member 660 may be molded such that the flexible valve member 660 may be in a substantially non-planar configuration in a relaxed state and in a compressed state, regardless of the relationship between a distal end of a cap (such as distal ends 35, 335 and caps 30, 330 shown in FIGS. 4 and 19) and the proximal end of the retainer or hub (such as proximal ends 42, 342, retainer 40 and hub 320 shown in FIGS. 4 and 19). However, the relationship between the distal end of a cap and the proximal end of a retainer and/or hub may affect the degree of non-planarity in the compressed state.

For example, as shown in FIG. 17, the distal end 662 and proximal end 663 are substantially coplanar (i.e. a first curved plane defined through the outer surface of the distal end 662 and a second curved plane defined through the outer surface of the proximal end 663 would not intersect) and/or non-planar (i.e. not parallel to a lateral plane, such as a flat plane perpendicular to and through the longitudinal axis of an introducer sheath into which the flexible valve member 660 is inserted, and/or not flat, for example, convex or concave) while in a relaxed state (i.e. not inserted into the introducer sheath, such as introducer sheath 10 shown in FIG. 4). The distal end 662 and proximal end 663 may be substantially coplanar and/or non-planar while in a compressed state (i.e. inserted into an introducer sheath (such as sheath 10, 110, 310, 810, 910)). Specifically, the distal end 662 and proximal end 663 may not intersect and/or may be convex or concave.

The opening 661 may have a varying cross-sectional dimension, such as the inner diameter, in the relaxed state. For example, as shown in FIG. 17, the opening 661 is substantially conical rather than cylindrical. The distal end 662 and proximal end 663 may be substantially coplanar and/or planar while in a retracted state (i.e. when inserted into a sheath but retracted proximally by a medical device (such as medical device 2)). The opening 661 may have a substantially constant cross-sectional dimension, such as the inner diameter, in the retracted state.

Although the opening 661 is shown as substantially conical, in FIG. 17, the opening 661 may have varying shapes. For example, for larger compressive stresses (or forces) on the distal end 662 or proximal end 663, the inner surfaces (not shown) of the opening 661 may be substantially abutting in the relaxed state near the end (i.e. distal end 662 or proximal end 663) with the larger compressive stresses (or forces). In embodiments where the compressive stresses (or forces) are induced in (or applied to) both the distal end and proximal end (such as distal end 62 and proximal end 63 shown in FIG. 4), whether those stresses (or forces) are induced in (or applied to) the distal end and proximal end through the molding processes (as in the flexible valve member 360) or through compression in the sheath, the inner surfaces of the opening 661 may be touching in the relaxed, compressed, retracted, other states, or combinations thereof.

The circumferential alignment of and/or offset between the distal engaging surface and the proximal engaging surface (such as proximal engaging surface 337 and distal engaging surface 347 shown in FIGS. 19-20) may affect the forces (or stresses) applied to (or induced in) the flexible valve member 660. The stresses (or forces) may be induced in (or applied to) only the proximal end 663 or the distal end 662, the stresses (or forces) may be unevenly induced in (or applied to) the proximal end 663 and/or the distal end 662, other stresses (or forces) may be induced in (or applied to) the proximal end 663 and/or the distal end 662, or combinations thereof.

Although the flexible valve member 660, in the present embodiment, may not include a proximal opening, the flexible valve member 660 may be retained by at least one of the hubs, retainers, caps, other introducer sheath components, or combinations thereof described herein. For example, the hub 320 (shown in FIG. 19) and the cap 330 (shown in FIG. 19) may be used to retain the flexible valve member 660 and/or provide a fluid tight seal between the introducer sheath 310 (shown in FIG. 19) and the flexible valve member 660. The material of the flexible valve member 660 may be sufficiently elastic and/or strong to be retained and/or to maintain the fluid tight seal. In other embodiments, the flexible valve member 660 and/or components of an introducer sheath (such as any introducer sheath described herein) may be varied to ensure proper retention and/or a fluid tight seal.

Referring to FIG. 18, the flexible valve member 760 may be formed in a manner similar to the flexible valve members 360, 460, 660. For example, the flexible valve member 760 may be molded such that the flexible valve member 760 may be in a substantially non-planar configuration in a relaxed state and in a compressed state, regardless of the relationship between a distal end of a cap (such as distal end 35, 335 and cap 30, 330 shown in FIGS. 4 and 19) and the proximal end of the retainer or hub (such as proximal end 42, 342, retainer 40, or hub 320 shown in FIGS. 4 and 19). However, the relationship between the distal end and the proximal end of an introducer sheath may affect the degree of non-planarity in the compressed state.

For example, as shown in FIG. 18, the distal end 762 and proximal end 763 are substantially coplanar (i.e. a first curved plane defined through the outer surface of the distal end 762 and a second curved plane defined through the outer surface of the proximal end 763 would not intersect) and/or non-planar (i.e. not parallel to a lateral plane, such as a flat plane perpendicular to and through the longitudinal axis of an introducer sheath into which the flexible valve member 760 may be inserted, and/or not flat, for example, convex or concave) while in a relaxed state (i.e. not inserted into the introducer sheath, such as introducer sheath 10 shown in FIG. 4). The distal end 762 and proximal end 763 may be substantially coplanar and/or non-planar while in a compressed state (i.e. inserted into an introducer sheath (such as sheath 10, 110, 310, 810, 910)). Specifically, the distal end 762 and proximal end 763 may not intersect and/or may be convex or concave.

The opening 761 may have a varying cross-sectional dimension, such as the inner diameter, in the relaxed state. For example, as shown in FIG. 18, the opening 761 is substantially conical rather than cylindrical. The distal end 762 and proximal end 763 may be substantially coplanar and/or planar while in a retracted state (i.e. when inserted into a sheath but retracted proximally by a medical device (such as medical device 2)). The opening 761 may have a substantially constant cross-sectional dimension, such as the inner diameter, in the retracted state.

Although the opening 761 is shown as substantially conical, in FIG. 18, the opening 761 may have varying shapes. For example, for larger compressive stresses (or forces) on the distal end 762 or proximal end 763, the inner surfaces (not shown) of the opening 761 may be substantially abutting in the relaxed state near the end (i.e. distal end 762 or proximal end 763) with the larger compressive stresses (or forces). In embodiments where the compressive stresses (or forces) are induced in (or applied to) both the distal end and proximal end (such as distal end 62 and proximal end 63 shown in FIG. 4), whether those stresses (or forces) are induced in (or applied to) the distal end and proximal end through the molding processes (as in the flexible valve member 360) or through compression in the sheath, the inner surfaces of the opening 761 may be touching in the relaxed, compressed, retracted, other states, or combinations thereof.

The circumferential alignment of and/or offset between the distal engaging surface and the proximal engaging surface (such as proximal engaging surface 337 and distal engaging surface 347 shown in FIGS. 19-20) may affect the forces (or stresses) applied to (or induced in) the flexible valve member 760. The stresses (or forces) may be induced in (or applied to) only the proximal end 763 or the distal end 762, the stresses (or forces) may be unevenly induced in (or applied to) the proximal end 763 and/or the distal end 762, other stresses (or forces) may be induced in (or applied to) the proximal end 763 and/or the distal end 762, or combinations thereof.

Although the flexible valve member 760, in the present embodiment, may not include a proximal opening or a distal opening, the flexible valve member 760 may be retained by at least one of the hubs, retainers, caps, other introducer sheath components, or combinations thereof described herein. For example, the hub 320 (shown in FIG. 19) and the cap 330 (shown in FIG. 19) may be used to retain the flexible valve member 760 and/or provide a fluid tight seal between the introducer sheath 310 (shown in FIG. 19) and the flexible valve member 760. The material of the flexible valve member 760 may be sufficiently elastic and/or strong to be retained and/or to maintain the fluid tight seal. In other embodiments, the flexible valve member 760 and/or components of an introducer sheath (such as any introducer sheath described herein) may be varied to ensure proper retention and/or a fluid tight seal.

Referring to FIGS. 21 and 22, FIGS. 21 and 22 illustrate additional embodiments of introducer sheaths 810, 910 with the flexible valve member 60 shown in FIGS. 2, 4, 6, and 8 in a compressed state. The introducer sheaths 810, 910 may be at least partially functionally similar to that of the introducer sheaths 10, 110, 310 previously described herein in most respects, wherein certain features will not be described in relation to these embodiments wherein those components may function in the manner as described above and are hereby incorporated into these alternative embodiments described below. Similarly, at least some aspects of introducer sheaths 810, 910 may be incorporated into other introducer sheaths described herein. For example, the caps 830, 930 of the introducer sheaths 810, 910 may be incorporated into the other introducer sheaths described herein. Like structures and/or components are given like reference numerals.

In the embodiment shown in FIGS. 21 and 21A, a cap 830 may be configured to cooperate with the proximal end 63 of the flexible membrane 60. In particular, in this embodiment, the exterior surface of the cap 830 may include a recess 831 formed therein which may be configured to receive the proximal end 63 of the flexible membrane 60.

The orientation of the flexible valve member 60 in a relaxed state, a compressed state, a retracted state, or combinations thereof, in some embodiments, may be determined by the relationship between the distal end 835 of the cap 830 and the proximal end 842 of the hub 820, as more clearly seen in the view of FIG. 21A. In other embodiments, the flexible membrane 360 may be configured to cooperate with a retainer (such as retainer 40 shown in FIG. 4) or other compound of the introducer sheath 310. As shown in FIG. 21, the cap 830 may include a proximal engaging surface 837 and the hub 320 may include a distal engaging surface 847. For example, the recess 831 and the aperture 833 of the cap 830 may form the proximal engaging surface 837 and the recess 845 and a lumen 844 of the hub 820 may form the distal engaging surface 847.

In some embodiments, the position of the proximal engaging surface 837 and the distal engaging surface 847 with respect to each other may determine the orientation of the flexible valve member 60 in a compressed and/or retracted state. In the present embodiment, the flexible valve member 60 may be in a substantially planar (i.e. flat) configuration in the relaxed state but in a substantially non-planar (i.e. not parallel to a lateral plane, such as a flat plane perpendicular to and through the longitudinal axis of the introducer sheath 810, and/or not flat, for example, convex or concave) configuration in the compressed state, based on the relationship between the distal end 835 of the cap 830 and the proximal end 842 of the hub 820.

In the present embodiment, the proximal engaging surface 837 and the distal engaging surface 847 may have substantially the same surface area. However, in the present embodiment, the proximal engaging surface 837 and the distal engaging surface 847 may be oriented to be offset from each other rather than mate with each other. For example, without the valve member 60, the proximal engaging surface 837 and distal engaging surface 847 would not substantially overlap each other when assembled. In another example, the proximal engaging surface 837 and distal engaging surface 847 may be circumferentially offset.

The proximal engaging surface 837 may include an outer edge 838 and/or an inner edge 839. The distal engaging surface 847 may include an outer edge 848 and/or an inner edge 849. In other embodiments, the proximal engaging surface 837 and/or distal engaging surface 847 may have a single edge and/or be otherwise configured to interact. For example, the proximal engaging surface 837 and/or distal engaging surface 847 may be substantially curved and/or otherwise configured.

The circumferential offset may include the circumferential offset of the outer edge 838 of the proximal engaging surface 837 with the outer edge 848 of the distal engaging surface 847 and/or the circumferential offset from the inner edge 839 of the proximal engaging surface 837 with the inner edge 849 of the distal engaging surface 847. As shown in FIG. 21, the outer edge 838 of the proximal engaging surface 837 is circumferentially offset from the outer edge 848 of the distal engaging surface 847 and/or the inner edge 839 of the proximal engaging surface 837 is circumferentially offset from the inner edge 849 of the distal engaging surface 847. For example, a dimension, such as a diameter, of the outer edge 838 of the proximal engaging surface 837 may be different from a dimension, such as a diameter, of the outer edge 848 of the distal engaging surface 847 and/or a dimension, such as a diameter, of the inner edge 839 of the proximal engaging surface 837 may be different from a dimension, such as a diameter, of the inner edge 849 of the distal engaging surface 847.

As shown in FIG. 21, the outer edge 838 of the proximal engaging surface 837 has a diameter that is smaller than a diameter of the outer edge 848 of the distal engaging surface 847 and the inner edge 839 of the proximal engaging surface 837 has a diameter that is smaller than a diameter of the inner edge 849 of the distal engaging surface 847. Furthermore, as shown in FIG. 21, the proximal engaging surface 837 and the distal engaging surface 847 do not overlap. For example, a dimension, such as a diameter, of the outer edge 838 of the proximal engaging surface 837 is smaller than a dimension, such as a dimension, of the inner edge 849 of the distal engaging surface 847. In other embodiments, the proximal engaging surface 837 and distal engaging surface 847 may be oriented such that they partially overlap. For example, the proximal engaging surface 837 and the distal engaging surface 847 may be circumferentially offset and may partially overlap.

The amount of the circumferential offset between the proximal engaging surface 837 and the distal engaging surface 847 may determine the effect on the planarity of the flexible valve member 60 in the compressed state. For example, if the proximal engaging surface 837 has a larger offset from the distal engaging surface 847 the flexible valve member 60 may be more non-planar (i.e. concave or convex), than if the proximal engaging surface 837 has a smaller offset from the distal engaging surface 847.

The circumferential alignment of and/or offset between the proximal engaging surface 837 and the distal engaging surface 847 may affect the forces (or stresses) applied to (or induced in) the flexible valve member 60. For example, the compressive force exerted on (or induced in) the flexible membrane 60 may be an axial compressive force (or stress) that may cause the opening 61 to be squeezed and thereby forming a more fluid tight seal therein. As shown in FIG. 2, the compressive forces (or stresses) may be generally applied to (or induced in) both the proximal end 63 and the distal end 62 of the flexible valve member 60. As shown in FIG. 21, a compressive stress (or force) may be generally induced in (or applied to) the proximal end 63 of the flexible valve member 60 while a tensile and/or axial stress (or force) may be generally induced in (or applied to) the distal end 62 of the flexible valve member 60.

In other embodiments, the stresses (or forces) may be induced in (or applied to) only the proximal end 63 or the distal end 62, the stresses (or forces) may be unevenly induced in (or applied to) the proximal end 63 and/or the distal end 62, other stresses (or forces) may be induced in (or applied to) the proximal end 63 and/or the distal end 62, or combinations thereof.

Referring to the embodiment shown in FIGS. 22 and 22A, a cap 930 may be configured to cooperate with the proximal end 63 of the flexible membrane 60. In particular, in this embodiment, the exterior surface of the cap 930 may include a recess 931 formed therein which may be configured to receive the proximal end 63 of the flexible membrane 60. The cap 930 may include a protrusion to be received within a corresponding cutout 915 formed on the exterior surface of the hub 920.

The orientation of the flexible valve member 60 in a relaxed state, a compressed state, a retracted state, or combinations thereof, in some embodiments, may be determined by the relationship between the distal end 935 of the cap 930 and the proximal end 942 of the hub 920, as more clearly seen in the view of FIG. 22A. As shown in FIG. 22, the cap 930 may include a proximal engaging surface 937 and the hub 920 may include a distal engaging surface 947. For example, the recess 931 and the aperture 933 of the cap 930 may form the proximal engaging surface 937 and the recess 945 and a lumen 944 of the hub 920 may form the distal engaging surface 947.

In some embodiments, the position of the proximal engaging surface 937 and the distal engaging surface 947 with respect to each other may determine the orientation of the flexible valve member 60 in a compressed or a retracted state. In the present embodiment, the flexible valve member 60 may be in a substantially planar (i.e. flat) configuration in the relaxed state but in a substantially non-planar (i.e. not parallel to a lateral plane, such as a flat plane perpendicular to and through the longitudinal axis of the introducer sheath 910, and/or not flat, for example, convex or concave) configuration in the compressed state, based on the relationship between the distal end 935 of the cap 930 and the proximal end 942 of the hub 920.

In the present embodiment, the proximal engaging surface 937 and the distal engaging surface 947 may have substantially the same surface area. However, in the present embodiment, the proximal engaging surface 937 and the distal engaging surface 947 may be oriented to be offset from each other rather than mate with each other. For example, without the valve member 60, the proximal engaging surface 937 and distal engaging surface 947 would not substantially overlap each other when assembled. In another example, the proximal engaging surface 937 and distal engaging surface 947 may be circumferentially offset.

The proximal engaging surface 937 may include an outer edge 938 and/or an inner edge 939. The distal engaging surface 947 may include an outer edge 948 and/or an inner edge 949. In other embodiments, the proximal engaging surface 937 and/or distal engaging surface 947 may have a single edge and/or be otherwise configured to interact. For example, the proximal engaging surface 937 and/or distal engaging surface 947 may be substantially curved and/or otherwise configured.

The circumferential offset may include the circumferential offset of the outer edge 938 of the proximal engaging surface 937 with the outer edge 948 of the distal engaging surface 947 and/or the circumferential offset from the inner edge 939 of the proximal engaging surface 937 with the inner edge 949 of the distal engaging surface 947. As shown in FIG. 22, the outer edge 938 of the proximal engaging surface 937 is circumferentially offset from the outer edge 948 of the distal engaging surface 947 and/or the inner edge 939 of the proximal engaging surface 937 is circumferentially offset from the inner edge 949 of the distal engaging surface 947. For example, a dimension, such as a diameter, of the outer edge 938 of the proximal engaging surface 937 may be different from a dimension, such as a diameter, of the outer edge 948 of the distal engaging surface 947 and/or a dimension, such as a diameter, of the inner edge 939 of the proximal engaging surface 937 may be different from a dimension, such as a diameter, of the inner edge 949 of the distal engaging surface 947.

As shown in FIG. 22, the outer edge 938 of the proximal engaging surface 937 has a diameter that is larger than a diameter of the outer edge 948 of the distal engaging surface 947 and the inner edge 939 of the proximal engaging surface 937 has a diameter that is larger than a diameter of the inner edge 949 of the distal engaging surface 947. Furthermore, as shown in FIG. 22, the proximal engaging surface 937 and the distal engaging surface 947 do not overlap. For example, a dimension, such as a diameter, of the inner edge 939 of the proximal engaging surface 937 is larger than a dimension, such as a dimension, of the outer edge 948 of the distal engaging surface 947. In other embodiments, the proximal engaging surface 937 and distal engaging surface 947 may be oriented such that they partially overlap. For example, the proximal engaging surface 937 and the distal engaging surface 947 may be circumferentially offset and may partially overlap.

The amount of the circumferential offset between the proximal engaging surface 937 and the distal engaging surface 947 may determine the effect on the planarity of the flexible valve member 60 in the compressed state.

The circumferential alignment of and/or offset between the proximal engaging surface 937 and the distal engaging surface 947 may affect the forces (or stresses) applied to (or induced in) the flexible valve member 60. As shown in FIG. 22, a compressive stress (or force) may be generally induced in (or applied to) the distal end 62 of the flexible valve member 60 while a tensile and/or axial stress (or force) may be generally induced in (or applied to) the proximal end 63 of the flexible valve member 60.

In other embodiments, the stresses (or forces) may be induced in (or applied to) only the proximal end 63 or the distal end 62, the stresses (or forces) may be unevenly induced in (or applied to) the proximal end 63 and/or the distal end 62, other stresses (or forces) may be induced in (or applied to) the proximal end 63 and/or the distal end 62, or combinations thereof.

Referring back to FIG. 21, the hub 820, the retainer (shown as 40 in FIG. 4), and the tubular member 850 may be integrally formed. In the present embodiment, the hub 820 and retainer (not shown) may be formed together and then be overmolded over the tubular member 850. In other embodiments, the hub 820, retainer, and tubular member 850 may be formed together. For example, the introducer sheath 810 may be formed according to the process described in connection with FIGS. 10 and 11A and 11B.

The introducer sheath 810 may include a shoulder area 827. The shoulder area 827 may be overmolded over a corresponding shelf portion 854 extending from a flared portion 853 of the introducer sheath 810 and/or a lock ring 890 may be used to retain the tubular member 850.

In the present embodiment, the introducer sheath 810, as shown in FIG. 19, may exclude a port (such as port 25 shown in FIGS. 3 and 6). In other embodiments, the introducer sheath 810 may include a port.

Similarly, as shown in FIG. 22, the hub 920, the retainer (shown as 40 in FIG. 4), and the tubular member 950 may be integrally formed. In the present embodiment, the hub 920 and retainer (not shown) may be formed together and then be overmolded over the tubular member 950. In other embodiments, the hub 920, retainer, and tubular member 950 may be formed together. For example, the introducer sheath 910 may be formed according to the process described in connection with FIGS. 10 and 11A and 11B.

The introducer sheath 910 may include a shoulder area 927. The shoulder area 927 may be overmolded over a corresponding shelf portion 954 extending from a flared portion 953 of the introducer sheath 910 and/or a lock ring 990 may be used to retain the tubular member 950.

In the present embodiment, the introducer sheath 910, as shown in FIG. 22, may exclude a port (such as port 25 shown in FIGS. 3 and 6). In other embodiments, the introducer sheath 910 may include a port.

Although the present invention has been described with regard to specific designs and materials, it shall not be considered limiting in any manner. For example, materials not described herein may be utilized as well as methods and processes.

Although the present invention has been described with regard to specific designs and materials, it shall not be considered limiting in any manner. For example, materials not described herein may be utilized as well as methods and processes.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An introducer sheath, comprising:
   a hub having a proximal end and a distal end and a lumen extending therebetween and a flexible valve member disposed in the proximal end of the hub, the flexible valve member having an aperture configured to receive a medical device, the flexible valve member having a proximal surface and a distal surface, both the proximal surface and the distal surface of the flexible valve member being transverse to a lateral plane through a longitudinal axis of the hub and both being non-planar in a relaxed state prior to insertion into the introducer sheath and planar in a retracted state within the introducer sheath, the non-planar profiles of the proximal surface and the distal surface being parallel in the relaxed state and the planar profiles of the proximal surface and the distal surface in the retracted state being parallel, and wherein the aperture has a substantially conical shape in the relaxed state and a substantially cylindrical shape in the retracted state; and
   an elongated tubular member having a proximal end and a distal end.

2. The introducer sheath of claim 1, wherein the flexible valve member is substantially concave in the relaxed state.

3. The introducer sheath of claim 1, further comprising a cap disposed adjacent the flexible valve member and coupled to the proximal end of the hub and wherein the cap is configured such that upon being disposed over the flexible valve member, the cap provides a compressive force to the flexible valve member which causes the flexible valve member to deform distally, thereby increasing the strength of the seal without reducing access to the lumen of the hub.

4. The introducer sheath of claim 1, wherein the flexible valve member has a substantially constant thickness in the relaxed state.

5. An introducer sheath, comprising:
   a hub having a proximal end and a distal end and a lumen extending therebetween and a flexible valve member disposed in the proximal end of the hub, the flexible valve member having an aperture configured to receive a medical device, the flexible valve member having a proximal surface and a distal surface, both the proximal surface and the distal surface of the flexible valve member being transverse to a lateral plane through a longitudinal axis of the hub and both being substantially non-planar in a relaxed state prior to introduction into the introducer sheath and planar in a retracted state within the introducer sheath, the non-planar profiles of the proximal surface and the distal surface being parallel in the relaxed state and the planar profiles of the proximal surface and the distal surface in the retracted state being parallel, and wherein the aperture has a substantially conical shape in the relaxed state and a substantially cylindrical shape in the retracted state;
   an elongated tubular member having a proximal end and a distal end; and
   a cap disposed adjacent the flexible valve member and coupled to the proximal end of the hub.

6. The introducer sheath of claim 5, wherein the flexible valve member is substantially concave in the relaxed state.

7. The introducer sheath of claim 5, wherein the cap is configured such that upon being disposed over the flexible valve member, the cap provides a compressive force to the flexible valve member which causes the aperture in the flexible valve member to be squeezed, thereby increasing the strength of the seal without reducing access to the lumen of the hub.

8. The introducer sheath of claim 5, wherein the flexible valve member has a substantially constant thickness in the relaxed state.

9. An introducer sheath, comprising:
   a hub having a proximal end and a distal end and a lumen extending therebetween and a flexible valve member disposed in the proximal end of the hub, the flexible valve member having an aperture configured to receive a medical device, the flexible valve member having a proximal surface and a distal surface, both the proximal surface and the distal surface of the flexible valve member being transverse to a lateral plane through a longitudinal axis of the hub and both being substantially non-planar in a relaxed state prior to introduction into the introducer sheath and planar in a retracted state within the introducer sheath, the non-planar profiles of the proximal surface and the distal surface being parallel in the relaxed state and the planar profiles of the proximal surface and the distal surface in the retracted state being parallel, and wherein the aperture has a substantially conical shape in the relaxed state and a substantially cylindrical shape in the retracted state, the hub having an inner diameter;
   an elongated tubular member having a proximal end and a distal end; and
   a cap disposed adjacent the flexible valve member and coupled to the proximal end of the hub, the cap including a recess configured to receive the proximal end of the flexible valve member having an outer diameter, the outer diameter of the recess being smaller than the inner diameter of the hub.

10. The introducer sheath of claim 9, wherein the cap is configured such that upon being disposed over the flexible valve member, the cap provides a compressive force to the flexible valve member which causes the flexible valve member to deform distally, thereby increasing the strength of the seal without reducing access to the lumen of the hub.

11. The introducer sheath of claim 10, wherein the compressive force provided by the cap to the flexible valve member is generated by the difference in the outer diameter of the recess of the cap and the inner diameter of the hub.

12. The introducer sheath of claim 9, wherein the cap is retained in a retained position by an adhesive, a snap fit, or combinations thereof.

13. The introducer sheath of claim 9, wherein the flexible valve member has a substantially constant thickness in the relaxed state.

14. An introducer sheath, comprising:
 a hub having a proximal end and a distal end and a lumen extending therebetween and a flexible valve member disposed in the proximal end of the hub, the flexible valve member having an aperture configured to receive a medical device, the flexible valve member having a proximal surface and a distal surface, both the proximal surface and the distal surface of the flexible valve member being transverse to a lateral plane through a longitudinal axis of the hub and both being substantially non-planar in a relaxed state prior to introduction into the introducer sheath and planar in a retracted state within the introducer sheath, the non-planar profiles of the proximal surface and the distal surface being parallel in the relaxed state and the planar profiles of the proximal surface and the distal surface in the retracted state being parallel, and wherein the aperture has a substantially conical shape in the relaxed state and a substantially cylindrical shape in the retracted state, the hub having an inner diameter, the hub being overmolded with an elongated tubular member having a proximal end and a distal end; and
 a cap disposed adjacent the flexible valve member and coupled to the proximal end of the hub, the cap including a recess configured to receive the proximal end of the flexible valve member having an outer diameter, the outer diameter of the recess being smaller than the inner diameter of the hub.

15. The introducer sheath of claim 14, wherein the flexible valve member has a substantially constant thickness in the relaxed state.

\* \* \* \* \*